United States Patent [19]

Teraji et al.

[11] Patent Number: 4,457,928
[45] Date of Patent: * Jul. 3, 1984

[54] CEPHEM COMPOUNDS

[75] Inventors: Tsutomu Teraji, Osaka; Kazuo Sakane; Amagasaki; Jiro Gota, Suita, all of Japan

[73] Assignee: Fujisawa Pharmaceutical Co., Ltd., Osaka, Japan

[*] Notice: The portion of the term of this patent subsequent to May 19, 1998 has been disclaimed.

[21] Appl. No.: 330,465

[22] Filed: Dec. 14, 1981

Related U.S. Application Data

[63] Continuation-in-part of Ser. No. 294,291, Aug. 19, 1981, , which is a continuation-in-part of Ser. No. 270,029, Jun. 3, 1981, Pat. No. 4,431,642.

[30] Foreign Application Priority Data

Dec. 1, 1980 [GB] United Kingdom ............... 8038456
Dec. 31, 1980 [GB] United Kingdom ............... 8041636
Apr. 9, 1981 [GB] United Kingdom ............... 8111164

[51] Int. Cl.$^3$ ................ A61K 31/545; C07D 501/46
[52] U.S. Cl. ................................ 424/246; 544/25
[58] Field of Search ................. 424/246; 544/25, 27

[56] References Cited

U.S. PATENT DOCUMENTS

| | | | |
|---|---|---|---|
| 4,264,595 | 4/1981 | Numata et al. | 544/25 |
| 4,278,671 | 7/1981 | Ochiai et al. | 544/25 |
| 4,332,800 | 6/1982 | Teraji et al. | 544/25 |
| 4,390,534 | 6/1983 | Teraji et al. | 544/27 |

Primary Examiner—Paul M. Coughlan, Jr.
Attorney, Agent, or Firm—Oblon, Fisher, Spivak, McClelland & Maier

[57] ABSTRACT

This invention relates to novel cephem compounds of high antimicrobial activity, to processes for preparation of said compounds, and to pharmaceutical compositions comprising said compounds, the novel cephem compounds being of the formula:

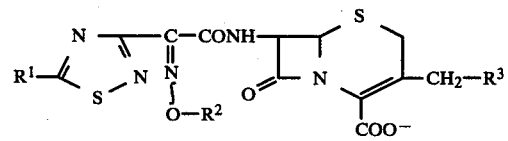

wherein
$R^1$ is amino or a protected amino group;
$R^2$ is hydrogen, lower aliphatic hydrocarbon group which may be substituted with a substituent selected from the group consisting of carboxy and protected carboxy, cyclo (lower) alkyl or cyclo (lower) alkenyl; and
$R^3$ is a thiazolio group which may be substituted with a substituent selected from the group consisting of lower alkyl and hydroxy (lower) alkyl, or a pyridinio group substituted with a substituent selected from the group consisting of halogen, cyano, hydroxy, amino, acylamino, lower alkanoyl, hydroxycarbamoyl, alkylcarbamoyl, carboxy, protected carboxy, lower alkyl, hydroxy (lower) alkyl, sulfo (lower) alkyl, protected amino (lower) alkyl, amino (lower) alkyl, carboxy (lower) alkyl and hydroxyimino (lower) alkyl;
and pharmaceutically acceptable salts thereof.

27 Claims, No Drawings

CEPHEM COMPOUNDS

This application is a continuation-in-part of parent application Ser. No. 294,291, filed Aug. 19, 1981, which in turn is a continuation-in-part of parent application Ser. No. 270,029, filed June 3, 1981 now U.S. Pat. No. 4,431,642.

The present invention relates to new cephem compounds and pharmaceutically acceptable salts thereof. More particularly, it relates to new cephem compounds and pharmaceutically acceptable salts thereof, which have antimicrobial activities and to processes for preparation thereof, to pharmaceutical composition comprising the same, and to a method of using the same therapeutically in the treatment of infectious diseases in human being and animals.

Accordingly, it is one object of the present invention to provide new cephem compounds and pharmaceutically acceptable salts thereof, which are active against a number of pathogenic microorganisms.

Another object of the present invention is to provide processes for the preparation of new cephem compounds and pharmaceutically acceptable salts thereof.

A further object of the present invention is to provide pharmaceutical composition comprising, as active ingredients, said new cephem compounds and pharmaceutically acceptable salts thereof.

Still further object of the present invention is to provide a method for the treatment of infectious diseases caused by pathogenic bacteria in human being and animals.

The object new cephem compounds are novel and can be represented by the following general formula (I).

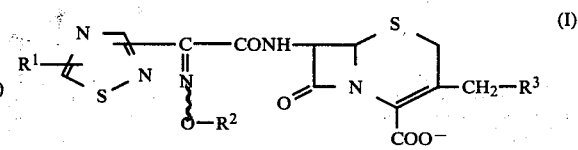

wherein
R$^1$ is amino or a protected amino group;
R$^2$ is hydrogen, lower aliphatic hydrocarbon group which may be substituted with suitable substituent(s), cyclo(lower)alkyl or cyclo(lower)alkenyl; and
R$^3$ is a thiazolio group which may be substituted with suitable substituent(s) or a pyridinio group substituted with substituent(s) selected from the group consisting of halogen, cyano, hydroxy, amino, acylamino, lower alkanoyl, hydroxycarbamoyl, alkylcarbamoyl, carboxy, protected carboxy, lower alkyl, hydroxy(lower)alkyl, sulfo(lower)alkyl, protected amino(lower)alkyl, amino(lower)alkyl, carboxy(lower)alkyl and hydroxyimino(lower)alkyl.

According to the present invention, the new cephem compounds (I) can be prepared by various processes which are illustrated in the following scheme.

Process 1

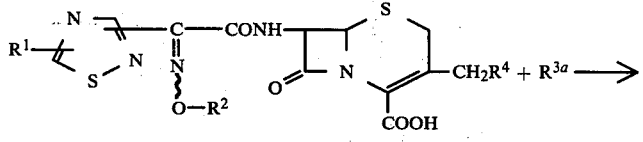

(II)
or a salt thereof (III)

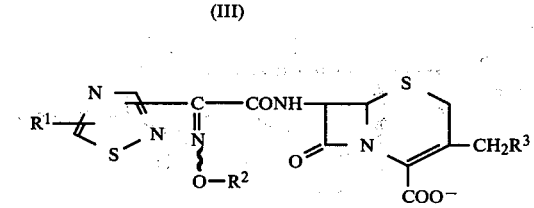

(I)
or a salt thereof

Process 2

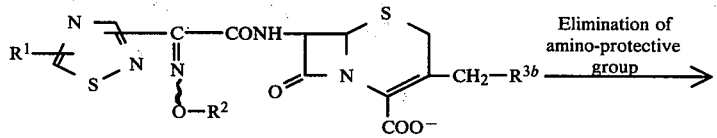

(Ia)
or a salt thereof

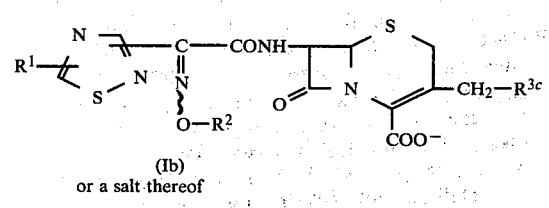

(Ib)
or a salt thereof

Process 3

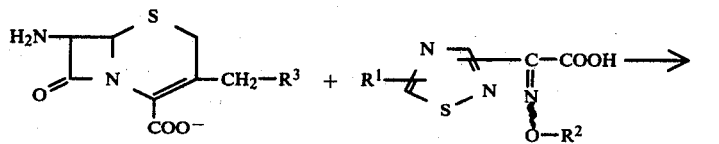

(IV)
or its reactive derivative
at the amino group or a
salt thereof.

(V)
or its reactive derivative
at the carboxy group
or a salt thereof

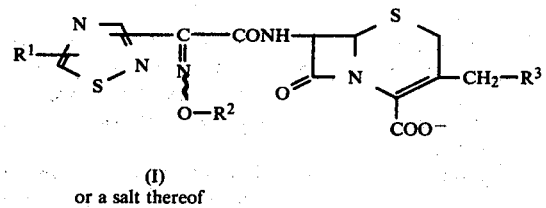

(I)
or a salt thereof

Process 4

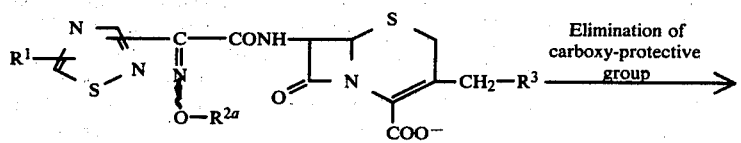

(Ic)
or a salt thereof

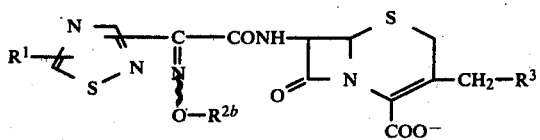

(Id)
or a salt thereof

Process 5

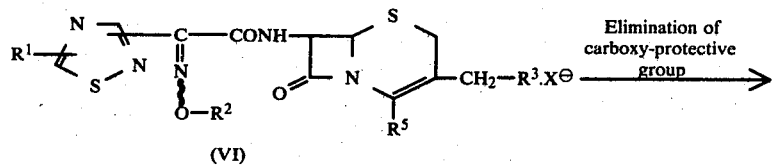

(VI)

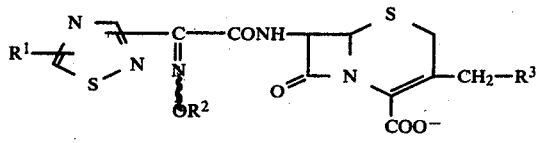

(I)
or a salt thereof wherein
$R^1$, $R^2$ and $R^3$ are each as defined above;
$R^4$ is a group which can be substituted with a group of the formula: $R^3$ wherein $R^3$ is as defined above;
$R^{3a}$ is thiazole which may be substituted with suitable substituent(s) or pyridine substituted with substituent(s) selected from the group consisting of halogen, cyano, hydroxy, acylamino, amino, lower alkanoyl, hydroxycarbamoyl, alkylcarbamoyl, carboxy, protected carboxy, lower alkyl, hydroxy(lower)alkyl, sulfo(lower)alkyl, protected amino(lower)alkyl, amino(lower)alkyl, carboxy(lower)alkyl and hydroxyimino(lower)alkyl;
$R^{3b}$ is a pyridino group substituted with protected amino(lower)alkyl or acylamino;
$R^{3c}$ is a pyridinio group substituted with amino(lower)alkyl or amino;
$R^{2a}$ is protected carboxy(lower)alkyl;
$R^{2b}$ is carboxy(lower)alkyl;
$R^5$ is a protected carboxy group; and
X is an acid residue.

Among the starting compounds of the present invention, the compound (VI) is novel and can be prepared by the following methods.

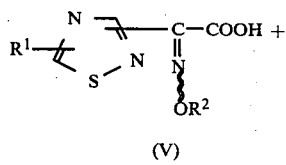

(V)

or its reactive derivative
at the carboxy group or a
salt thereof

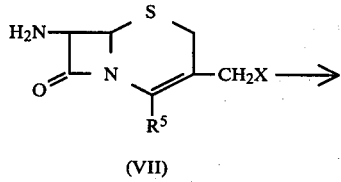

(VII)

or its reactive derivative
at the amino group or a salt
thereof

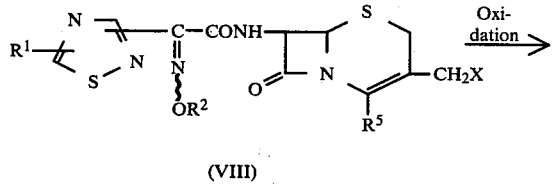

(VIII)

or a salt thereof

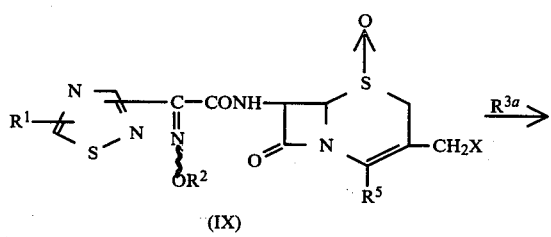

(IX)

or a salt thereof

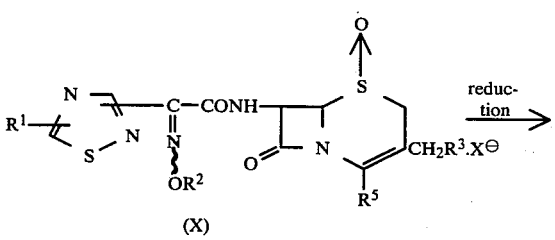

(X)

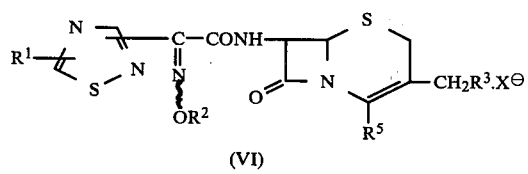

(VI)

wherein $R^1$, $R^2$, $R^3$, $R^{3a}$, $R^5$ and X are each as defined above.

Regarding the object compounds (I), (Ia), (Ib), (Ic) and (Id) and the starting compounds (II), (V), (VIII), (VI), (IX) and (X), it is to be understood that said object and starting compounds include syn isomer, anti isomer and a mixture thereof. For example, with regard to the object compound (I), syn isomer means one geometrical isomer having the partial structure represented by the following formula:

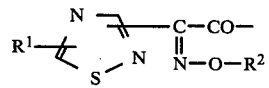

(wherein $R^1$ and $R^2$ are each as defined above) and anti isomer means the other geometrical isomer having the partial structure represented by the following formula:

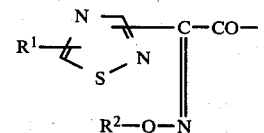

(wherein $R^1$ and $R^2$ are each as defined above).

Regarding the other object compounds and starting compounds as mentioned above, the syn isomer and the anti isomer can also be referred to the same geometrical isomers as illustrated for the compound (I).

Suitable pharmaceutically acceptable salts of the object compounds (I) are conventional non-toxic salt and include a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), an organic acid salt (e.g. acetate, maleate, tartrate, methanesulfonate, benzenesulfonate, formate, toluenesulfonate, etc.), an inorganic acid salt (e.g. hydrochloride, hydrobromide, hydroiodide, sulfate, phosphate, etc.), or a salt with an amino acid (e.g. arginine, aspartic acid, glutamic acid, etc.), and the like.

In the above and subsequent descriptions of the present specification, suitable examples and illustrations of the various definitions which the present invention include within the scope thereof are explained in details as follows.

The term "lower" is intended to mean 1 to 6 carbon atoms, unless otherwise indicated.

Suitable "protected amino" for $R^1$ and "protected amino" moiety in the term "protected amino(lower)alkyl" may include an acylamino or an amino group substituted by a conventional protecting group such as ar(lower)alkyl which may have at least one suitable substituent(s), (e.g. benzyl, trityl, etc.) or the like.

Suitable acyl moiety in the term "acylamino" may include carbamoyl, aliphatic acyl group and acyl group containing an aromatic or heterocyclic ring. And, suitable examples of the said acyl may be lower alkanoyl (e.g. formyl, acetyl, propionyl, butyryl, isobutyryl, valeryl, isovaleryl, oxalyl, succinyl, pivaloyl, etc.); lower alkoxycarbonyl having 2 to 7 carbon atoms (e.g. methoxycarbonyl, ethoxycarbonyl, propoxycarbonyl, 1-cyclopropylethoxycarbonyl, isopropoxycarbonyl, butoxycarbonyl, tertiarybutoxycarbonyl, pentyloxycarbonyl, hexyloxycarbonyl, etc.); lower alkanesulfonyl (e.g. mesyl, ethanesulfonyl, propanesulfonyl, isopropanesulfonyl, butanesulfonyl, etc.); arenesulfonyl (e.g. benzenesulfonyl, tosyl, etc.); aroyl (e.g. benzoyl, toluoyl, xyloyl, naphthoyl, phthaloyl, indancarbonyl, etc.); ar(lower)alkanoyl (e.g. phenylacetyl, phenylpropionyl, etc.); ar(lower)alkoxycarbonyl (e.g. benzyloxycarbonyl, phenethyloxycarbonyl, etc.), and the like. The acyl moiety as stated above may have at least one suitable substituent(s) such as halogen (chlorine, bromine, fluorine and iodine), lower alkanoyl, carboxy or the like.

Suitable lower aliphatic hydrocarbon group may include lower alkyl, lower alkenyl, lower alkynyl and the like.

Suitable "cyclo(lower)alkyl" for $R^2$ may include one having 3 to 6 carbon atoms, for example, cyclopropyl, cyclobutyl, cyclopentyl, cyclohexyl or the like, preferably one having 4 to 6 carbon atoms.

Suitable "cyclo(lower)alkenyl" for $R^2$ may include one having 3 to 6 carbon atoms, for example, cyclopentenyl, cyclohexenyl or the like, preferably one having 5 to 6 carbon atoms.

Suitable "lower alkyl" and "lower alkyl" moiety in the terms "hydroxy(lower)alkyl", "sulfo(lower)alkyl", "protected amino(lower)alkyl", "hydroxyimino(lower)alkyl", "amino(lower)alkyl", "protected carboxy(lower)alkyl" and "carboxy(lower)alkyl" is one having 1 to 6 carbon atom(s) and may include methyl, ethyl, propyl, isopropyl, butyl, isobutyl, tert-butyl, pentyl, tert-pentyl, hexyl and the like, and preferably one having 1 to 4 carbon atom(s).

Suitable "lower alkenyl" is one having 2 to 6 carbon atoms and may include vinyl, allyl, isopropenyl, 1-propenyl, 2-butenyl, 3-pentenyl and the like.

Suitable "lower alkynyl" is one having 2 to 6 carbon atoms and may include ethynyl, 2-propynyl, 2-butynyl, 3-pentynyl, 3-hexynyl and the like.

The lower aliphatic hydrocarbon group as mentioned above may be substituted with 1 to 3 suitable substituent(s) such as carboxy, protected carboxy as mentioned below, halogen (e.g. chlorine, bromine, etc.) or the like.

Suitable substituent(s) on a thiazolio group for $R^3$ and thiazole for $R^{3a}$ may include lower alkyl (e.g. methyl, ethyl, propyl, isopropyl, butyl, isobutyl, tert-butyl, pentyl, tert-pentyl, hexyl, etc.), hydroxy(lower)alkyl (e.g. hydroxymethyl, hydroxyethyl, hydroxypropyl, hydroxybutyl, etc.) and the like, and the number of the substituent(s) may be 1 to 3.

A pyridinio group for $R^3$ or pyridine for $R^{3a}$ is substituted with 1 to 3 substituent(s) as mentioned above.

Suitable "halogen" may include chlorine, bromine, fluorine and iodine.

Suitable "lower alkanoyl" can be referred to the ones as exemplified for aforesaid "acyl".

Suitable "alkyl" moiety in the term "alkylcarbamoyl" is one having 1 to 14 carbon atom(s) and may include methyl, ethyl, propyl, isopropyl, butyl, isobutyl, t-butyl, pentyl, t-pentyl, hexyl, heptyl, octyl, nonyl, decyl, undecyl, dodecyl, tridecyl, tetradecyl and the like, preferably one having 1 to 12 carbon atom(s).

Suitable "protected carboxy" and "protected carboxy" moiety in the term "protected carboxy(lower)alkyl" may include esterified carboxy in which said ester may be the ones such as alkyl ester (e.g. methyl ester, ethyl ester, propyl ester, isopropyl ester, butyl ester, isobutyl ester, t-butyl ester, pentyl ester, t-pentyl ester, hexyl ester, heptyl ester, octyl ester, nonyl ester, decyl ester, undecyl ester, dodecyl ester, hexadecyl ester, etc.); lower alkenyl ester (e.g. vinyl ester, allyl ester, etc.); lower alkynyl ester (e.g. ethynyl ester, propynyl ester, etc.); mono(or di or tri)-halo(lower)alkyl ester (e.g., 2-iodoethyl ester, 2,2,2-trichloroethyl ester, etc.); lower alkanoyloxy(lower)alkyl ester (e.g. acetoxymethyl ester, propionyloxymethyl ester, 1-acetoxypropyl ester, valeryloxymethyl ester, pivaloyloxymethyl ester, hexanoyloxymethyl ester, 1-acetoxyethyl ester, 2-propionyloxyethyl ester, 1-isobutyryloxyethyl ester, etc.); lower alkanesulfonyl(lower)alkyl ester (e.g., mesylmethyl ester, 2-mesylethyl ester, etc.); ar(lower)alkyl ester, for example, phenyl(lower)alkyl ester which may be substituted with one or more suitable substituent(s) (e.g. benzyl ester, 4-methoxybenzyl ester, 4-nitrobenzyl ester, phenethyl ester, trityl ester, diphenylmethyl ester, bis(methoxyphenyl)methyl ester, 3,4-dimethoxybenzyl ester, 4-hydroxy-3,5-ditertiarybutylbenzyl ester, etc.); lower alkoxycarbonyloxy(lower)alkyl ester (e.g. methoxycarbonyloxymethyl ester, ethoxycarbonyloxymethyl ester, ethoxycarbonyloxyethyl ester, etc.) which may be substituted with azido; a heterocyclic ester, preferably benzotetrahydrofuryl ester which may be substituted with oxo group, more preferably phthalidyl ester; aroyloxy(lower)alkyl ester (e.g. benzoyloxymethyl ester, benzoyloxyethyl ester, toluoyloxyethyl ester, etc.); aryl ester which may have one or more suitable substituent(s) (e.g. phenyl ester, tolyl ester, tertiarybutylphenyl ester, xylyl ester, mesityl ester, cumenyl ester, etc.), and the like. Preferable example of "protected carboxy" may be alkoxycarbonyl (e.g. methoxycarbonyl, ethoxycarbonyl, propoxycarbonyl, isopropoxycarbonyl, butoxycarbonyl, t-butoxycarbonyl, pentyloxycarbonyl, hexyloxycarbonyl, heptyloxycarbonyl, octyloxycarbonyl, nonyloxycarbonyl, decyloxycarbonyl, undecyloxycarbonyl, dodecyloxycarbonyl, hexadecyloxycarbonyl, etc.).

Suitable $R^4$ may include an acid residue such as acyloxy, azido, halogen or the like, wherein acyl moiety in the term "acyloxy" and halogen can be referred to the ones as exemplified above.

Suitable X may include acid residue as above.

Preferred embodiments of the object compound (I) are as follows.

Preferred embodiment of $R^1$ is amino; $R^2$ is lower alkyl, lower alkynyl, lower alkenyl, cyclo(lower)alkyl (most preferably cyclopentyl), cyclo(lower)alkenyl (most preferably cyclopentenyl), carboxy(lower)alkyl or esterified carboxy(lower)alkyl (more preferably lower alkoxycarbonyl(lower)alkyl); $R^3$ is thiazolio, thiazolio substituted with lower alkyl and hydroxy(lower)alkyl, or pyridinio substituted with 1 to 2 substituent(s) selected from the group consisting of halogen, cyano, hydroxy, lower alkanoyl (most preferably acetyl), acylamino (more preferably lower alkanesulfonylamino or lower alkanoylamino which may be substituted with carboxy), amino, hydroxycarbamoyl, alkylcarbamoyl, carboxy, alkoxycarbonyl, lower alkyl, hydroxy(lower)alkyl, carboxy(lower)alkyl, amino(lower)alkyl, lower alkoxycarbonylamino(lower)alkyl, lower alkanoylamino(lower)alkyl, sulfo(lower)alkyl and hydroxyimino(lower)alkyl.

The processes for preparing the object compounds of the present invention are explained in details in the following.

Process 1

The object compound (I) or a salt thereof can be prepared by reacting the compound (II) or a salt thereof with the compound (III).

Suitable salt of the compound (II) can be referred to the ones exemplified for the compound (I).

The present reaction may be carried out in a solvent such as water, phosphate buffer, acetone, chloroform, acetonitrile, nitrobenzene, methylene chloride, ethylene chloride, formamide, dimethylformamide, methanol, ethanol, ether, tetrahydrofuran, dimethylsulfoxide, or any other organic solvent which does not adversely affect the reaction, preferably in ones having strong polarities. Among the solvents, hydrophilic solvents may be used in a mixture with water. The reaction is preferably carried out in around neutral medium. When the compound (II) is used in a free form, the reaction is preferably conducted in the presence of a base, for example, inorganic base such as alkali metal hydroxide, alkali metal carbonate, alkali metal bicarbonate, organic base such as trialkylamine, and the like. The reaction temperature is not critical, and the reaction is usually carried out at ambient temperature, under warming or under heating. The present reaction is preferably carried out in the presence of alkali metal halide (e.g. sodium iodide, potassium iodide, etc.), alkali metal thiocyanate (e.g. sodium thiocyanate, potassium thiocyanate, etc.) etc.

Process 2

The object compound (Ib) or a salt thereof can be prepared by subjecting the compound (Ia) or a salt thereof to elimination reaction of the protective group of amino.

Suitable salts of the compounds (Ia) and (Ib) can be referred to the ones exemplified for the compound (I).

The present elimination reaction is carried out in accordance with a conventional method such as hydrolysis; reduction; a method by reacting the compound (Ia) wherein the protective group is acyl group with imino-halogenating agent and then with iminoetherifying agent, and, if necessary, subjecting the resulting compound to hydrolysis; or the like. The hydrolysis may include a method using an acid or base or hydrazine and the like. These methods may be selected depending on the kind of the protective groups to be eliminated.

Among these methods, hydrolysis using an acid is one of the common and preferable method for eliminating the protective group such as substituted or unsubstituted alkoxycarbonyl (e.g. t-pentyloxycarbonyl, t-butoxycarbonyl, etc.), alkanoyl (e.g. formyl, etc.), cycloalkoxycarbonyl, substituted or unsubstituted aralkoxycarbonyl (e.g. benzyloxycarbonyl, substituted benzyloxycarbonyl, etc.), ar(lower)alkyl (e.g. benzyl, trityl, etc.) or the like.

Suitable acid may include an organic or an inorganic acid, for example, formic acid, trifluoroacetic acid, benzenesulfonic acid, p-toluenesulfonic acid, hydrochloric acid and the like, and preferable acid is, for example, formic acid, trifluoroacetic acid, hydrochloric acid, etc. The acid suitable for the reaction can be selected according to the kind of protective group to be eliminated. When the elimination reaction is conducted with the acid, it can be carried out in the presence or absence of a solvent. Suitable solvent may include a conventional organic solvent, water or a mixture thereof. When trifluoroacetic acid is used, the elimination reaction may preferably be carried out in the presence of anisole.

The hydrolysis using hydrazine is commonly applied for eliminating the protective group, for example, succinyl or phthaloyl.

The hydrolysis with a base is preferably applied for eliminating acyl group, for example, haloalkanoyl (e.g. dichloroacetyl, trifluoroacetyl, etc.) etc. Suitable base may include, for example, an inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkali metal acetate (e.g. sodium acetate, potassium acetate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), or the like, and an organic base such as trialkylamine (e.g. trimethylamine, triethylamine, etc.), picoline, N-methylpyrrolidine, N-methylmorpholine, 1,5-diazabicyclo[4,3,0]non-5-ene, 1-4-diazabicyclo[2,2,2]octane, 1,5-diazabicyclo[5,4,0]undecene-5 or the like. The hydrolysis using a base is often carried out in water, a conventional organic solvent or a mixture thereof.

Among the protective group, the acyl group can be generally eliminated by hydrolysis as mentioned above or by the other conventional hydrolysis. In case that the acyl group is halogen substituted-alkoxycarbonyl or 8-quinolyloxycarbonyl, they are eliminated by treating with a heavy metal such as copper, zinc or the like.

The reductive elimination is generally applied for eliminating the protective group, for example, haloalkoxycarbonyl (e.g. trichloroethoxycarbonyl, etc.), substituted or unsubstituted aralkoxycarbonyl (e.g. benzyloxycarbonyl, substituted benzyloxycarbonyl etc.), 2-pyridylmethoxycarbonyl, etc. Suitable reduction may include, for example, reduction with an alkali metal borohydride (e.g. sodium borohydride, etc.) and the like.

The reaction temperature is not critical and may be suitably selected in accordance with the kind of the protective group of the amino group and the elimination method as mentioned above, and the present reaction is preferably carried out under a mild condition such as under cooling, at ambient temperature or slightly elevated temperature.

The present reaction includes, within its scope, the cases that the protected amino group for $R^1$ is transformed into the free amino group in the course of the elimination reaction as mentioned above or in the post-treatment of the reaction mixture of reaction product.

Process 3

The object compound (I) or a salt thereof can be prepared by reacting the compound (IV) or its reactive derivative at the amino group or a salt thereof with the compound (V) or its reactive derivative at the carboxy group or a salt thereof.

Suitable reactive derivative at the amino group of the compound (IV) may include conventional reactive derivative used in amidation, for example, Schiff's base type imino or its tautomeric enamine type isomer formed by the reaction of the compound (IV) with a carbonyl compound; a silyl derivative formed by the reaction of the compound (IV) with a silyl compound such as bis(trimethylsilyl)acetamide, trimethylsilylacetamide or the like; a derivative formed by reaction of the compound (IV) with phosphorus trichloride or phosgene, and the like.

Suitable salt of the compound (IV) may include an acid addition salt such as an organic acid salt (e.g. acetate, maleate, tartrate, benzenesulfonate, toluenesulfonate, etc.) or an inorganic acid salt (e.g. hydrochloride, hydrobromide, sulfate, phosphate, etc.); a metal salt (e.g. sodium salt, potassium salt, calcium salt, magnesium salt, etc.); ammonium salt; an organic amine salt (e.g. triethylamine salt, dicyclohexylamine salt, etc.), and the like.

Suitable reactive derivative at the carboxy group of the compound (V) may include an acid halide, an acid anhydride, an activated amide, an activated ester, and the like. The suitable example may be an acid chloride; an acid azide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkylcarbonic acid, aliphatic carboxylic acid (e.g. pivalic acid, pentanoic acid, isopentanoic acid, 2-ethylbutyric acid, acetic acid or trichloroacetic acid, etc.) or aromatic carboxylic acid (e.g. benzoic acid, etc.); a symmetrical acid anhydride; an activated amide with imidazole, dimethylpyrazole, triazole or tetrazole; or an activated ester (e.g. cyanomethyl ester, methoxymethyl ester, dimethyliminomethyl [$(CH_3)_2N^+=CH-$] ester, vinyl ester, propargyl ester, p-nitrophenyl ester, 2,4-dinitrophenyl ester, trichlorophenyl ester, pentachlorophenyl ester, mesyl phenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, or an ester with N,N-dimethylhydroxylamine, 1-hydroxy-2-(1H)-pyridone, N-hydroxysuccinimide, N-hydroxyphthalimide or 1-hydroxy-6-chloro-1H-benzotriazole, and the like. These reactive derivatives can be optionally selected from them according to the kind of the compound (V) to be used.

The salts of the compound (V) may be salts with an inorganic base such as an alkali metal salts (e.g. sodium or potassium salt), or an alkaline earth metal salt (e.g. calcium or magnesium salt), a salt with an organic base such as trimethylamine, triethylamine, pyridine, a salt with an acid (e.g. hydrochloric acid or hydrobromic acid) or the like.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvent which does not adversely influence to the reaction. Among these solvents, hydrophilic solvents may be used in a mixture with water.

When the compound (V) is used in free acid form or its salts form in the reaction, the reaction is preferably carried out in the presence of a conventional condensing agent such as N,N-dicyclohexylcarbodiimide; N-cyclohexyl-N'-morpholinoethylcarbodiimide; N-cyclohexyl-N'-(4-diethylaminocyclohexyl)carbodiimide; N,N-diethylcarbodiimide; N,N,diisopropylcarbodiimide; N-ethyl-N'-(3-dimethylaminopropyl)carbodiimide; N,N-carbonylbis(2-methylimidazole); pentamethylene-ketene-N-cyclohexylimine; diphenylketene-N-cyclohexylimine; ethoxyacetylene; ethyl polyphosphate; isopropyl polyphosphate; diethyl phosphorochloridite; phosphorus oxychloride; phosphorus trichloride; phosphorus pentachloride; thionyl chloride; oxalyl chloride; triphenylphosphine; N-ethyl-7-hydroxybenzisoxazolium fluoroborate; N-ethyl-5-phenylisoxazolium-3'-sulfonate; 1-(p-chlorobenzenesulfonyloxy)-6-chloro-1H-benzotriazole; so-called Vilsmeier reagent, for example (chloromethylene) dimethylammonium chloride produced by the reaction of dimethylformamide with thionyl chloride or phosgene, a compound produced by the reaction of dimethylformamide with phosphorus oxychloride, etc.; or the like.

The reaction may be also carried out in the presence of an inorganic or an organic base such as an alkali metal hydroxide, an alkali metal bicarbonate, alkali metal carbonate, alkali metal acetate, tri(lower)alkylamine, pyridine, N-(lower)alkylmorpholine, N,N-di(lower)alkylbenzylamine, N,N-di(lower)alkylaniline as exemplified below, or the like. When the base or the condensing agent is in liquid, it can be used also as a solvent. The reaction temperature is not critical, and the reaction is usually carried out under cooling or at ambient temperature.

In the present reaction, a syn-isomer of the object compound (I) can be obtained preferably by conducting the reaction of the compound (IV) with a synisomer of the starting compound (V).

Process 4

The object compound (Id) or a salt thereof can be prepared by subjecting the compound (Ic) or a salt thereof to elimination reaction of the protective group of carboxy.

Suitable salt of the compounds (Ic) and (Id) can be referred to the ones exemplified for the compound (I).

The present reaction is carried out in accordance with a conventional method such as hydrolysis, reduction or the like.

In case that the protective group is an ester, the protective group can be eliminated by hydrolysis. Hydrolysis is preferably carried out in the presence of a base or an acid. Suitable base may include an inorganic base and an organic base such as an alkali metal (e.g. sodium, potassium, etc.), an alkaline earth metal (e.g. magnesium, calcium, etc.), the hydroxide or carbonate or bicarbonate thereof, trialkylamine (e.g. trimethylamine, triethylamine, etc.), picoline, 1,5-diazabicyclo[4,3,0]-none-5-ene, 1,4-diazabicyclo[2,2,2]octane, 1,8-diazabicyclo[5,4,0]undecene-7, or the like. Suitable acid may include an organic acid (e.g. formic acid, acetic acid, propionic acid, trifluoroacetic acid, etc.) and an inorganic acid (e.g. hydrochloric acid, hydrobromic acid, sulfuric acid, etc.).

The reaction is usually carried out in a solvent such as water, an alcohol (e.g. methanol, ethanol, etc.), a mixture thereof or any other solvent which does not adversely influence to the reaction. A liquid base or acid can be also used as the solvent. The reaction temperature is not critical and the reaction is usually carried out under cooling to warming.

Reduction can be applied preferably for elimination of the protective group such as 4-nitrobenzyl, 2-iodoethyl, 2,2,2-trichloroethyl, or the like. The reduction method applicable for the elimination reaction may include, for example, reduction by using a combination of a metal (e.g. zinc, zinc amalgam, etc.) or a salt of chrome compound (e.g. chromous chloride, chromous acetate, etc.) and an organic or inorganic acid (e.g. acetic acid, propionic acid, hydrochloric acid, etc.); and conventional catalytic reduction in the presence of a conventional metallic catalyst (e.g. palladium-carbon, etc.).

Process 5

The compound (I) or a salt thereof can be prepared by subjecting the compound (VI) to elimination reaction of carboxy-protective group.

The present elimination reaction can be carried out according to a similar manner to that of Process 4.

The Preparations of the starting compound (VI) are explained in detail in the following.

Preparation 1

The compound (VIII) can be prepared by reacting the compound (V) or its reactive derivative at the carboxy group or a salt thereof with the compound (VII) or its reactive derivative at the amino group or a salt thereof.

The present reaction can be carried out in a similar manner to that of Process 3.

Preparation 2

The compound (IX) or a salt thereof can be prepared by oxidizing the compound (VIII) or a salt thereof.

Suitable oxidizing agent to be used in this reaction may include all oxidizing agent which can oxidize —S— group in cephalosporin compounds to

group, for example, peroxide (e.g., hydrogen peroxide, 3-chloroperbenzoic acid, etc.) and the like.

The reaction is usually carried out in solvent such as methylene chloride or any other solvent which does not adversely affect the reaction. The reaction temperature is not critical and preferably under cooling or at ambient temperature.

Preparation 3

The compound (X) can be prepared by reacting the compound (IX) or a salt thereof with the compound $R^{3a}$.

The reaction can be carried out according to a similar manner to that of Process 1.

Preparation 4

The compound (VI) can be prepared by reducing the compound (X).

The present reduction can be carried out in the presence of conventional reducing agent which can reduce

group in cephalosporin compound to —S— group, for example, phosphorus halide such as phosphorus trihalide (e.g., phosphorus trichloride, etc.).

The object compound (I) of the present invention exhibits high antimicrobial activity and inhibits the growth of a number of microorganisms including pathogenic Gram-positive and Gram-negative bacteria.

For therapeutic administration, the cephalosporin compounds according to the present invention are used in the form of pharmaceutical preparation which contain said compounds in admixture with a pharmaceutically acceptable carriers such as an organic or inorganic solid or liquid excipient suitable for oral, parenteral or external administration. The pharmaceutical preparations may be in solid form such as capsule, tablet, dragee, ointment or suppository, or in liquid form such as solution, suspension, or emulsion. If desired, there may be included in the above preparations auxiliary substances, stabilizing agents, wetting or emulsifying agents, buffers and other commonly used additives.

While the dosage of the compounds may vary from and also depend upon the age and condition of the patient, an average single dose of about 50 mg., 100 mg., 250 mg., and 500 mg. of the compounds according to the present invention has proved to be effective for treating of infectious diseases caused by a number of pathogenic bacteria. In general amounts, daily dose between 1 mg/body and about 1000 mg/body or even more may be administered.

Now in order to show the utility of the object compounds (I), test data on anti-microbial activity of representative compounds of the present invention are shown below.

Test method

One loopful of an overnight culture of each test strain in Trypticase-soy broth ($10^8$ viable cells per ml.) was streaked on heart infusion agar (HI-agar) containing graded concentrations of antibiotics, and the minimal inhibitory concentration (MIC) was expressed in terms of μg/ml after incubation at 37° C. for 20 hours.

Test compound (1) 7-[2-Ethoxyimino-2-(5-amino-1,2,4-thiadiazol-3-yl)acetamido]-3-(3-hydroxymethyl-1-pyridiniomethyl)-3-cephem-4-carboxylate (syn isomer)

(2) 7-[2-Ethoxyimino-2-(5-amino-1,2,4-thiadiazol-3-yl)acetamido]-3-(4-hydroxymethyl-1-pyridiniomethyl)-3-cephem-4-carboxylate (syn isomer)

(3) 7-[2-Ethoxyimino-2-(5-amino-1,2,4-thiadiazol-3-yl)acetamido]-3-(3-chloro-1-pyridiniomethyl)-3-cephem-4-carboxylate (syn isomer)

(4) 7-[2-Ethoxyimino-2-(5-amino-1,2,4-thiadiazol-3-yl)acetamido]-3-(3,5-dimethyl-1-pyridiniomethyl)-3-cephem-4-carboxylate (syn isomer)

(5) 7-[2-Ethoxyimino-2-(5-amino-1,2,4-thiadiazol-3-yl)acetamido]-3-[4-(3-hydroxypropyl)-1-pyridiniomethyl]-3-cephem-4-carboxylate (syn isomer)

Test Results

| Test Bacteria | MIC (μg/ml) Test Compound | | | | |
|---|---|---|---|---|---|
| | (1) | (2) | (3) | (4) | (5) |
| B. subtilis ATCC 6633 | 0.78 | 0.78 | 0.78 | 1.56 | 0.78 |
| Ps. aeruginosa 2 | 6.25 | 12.50 | 6.25 | 6.25 | 12.50 |
| S. marcescens 35 | 3.13 | 1.56 | 3.13 | 3.13 | 1.56 |

The following Preparations and Examples are given for the purpose of illustrating the present invention.

Preparation 1

To a suspension of isonicotinoyl chloride hydrochloride (8.94 g) in methylene chloride (50 ml) was dropped a solution of t-butylamine (11.0 g) in methylene chloride (30 ml) over 70 minutes below 40° C. under stirring. The mixture was stirred for 4 hours at ambient temperature and poured into water. After the mixture was adjusted to pH 7.5 with aqueous sodium bicarbonate, the organic layer was separated out, washed with water, dried over magnesium sulfate and evaporated to dryness to give N-t-butylisonicotinamide (6.8 g), mp. 115° C. to 117° C.

IR (Nujol): 3270, 1638, 1595, 1544, 1317, 1210 cm$^{-1}$
NMR (DMSO-d$_6$, δ): 1.40 (9H, s), 7.7 (2H, m), 8.05 (1H, bs), 8.7 (2H, m)

Preparation 2

The following compounds were obtained according to a similar manner to that of Preparation 1.
(1) N-Octylisonicotinamide, mp 61° to 63° C.
IR (Nujol): 3290, 1630, 1595, 1538, 1310, 1290 cm$^{-1}$
(2) N-Dodecylisonicotinamide, mp 71° to 74° C.
IR (Nujol): 3400, 3320, 1630, 1598, 1535 cm$^{-1}$ Preparation 3

A mixture of isonicotinoyl chloride hydrochloride (17.8 g), t-butylalcohol (14.8 g) and 4-(N,N-dimethylamino)pyridine (122 mg) in methylene chloride (200 ml) was refluxed for 6 hours. The mixture was washed with aqueous sodium bicarbonate and water, dried over magnesium sulfate and evaporated to give oily t-butyl isonicotinate (8.3 g).

IR (film): 2950, 2830, 1720, 1580, 1560, 1410, 1365, 1320, 1290, 1145, 1120 cm$^{-1}$
NMR (DMSO-d$_6$, δ): 1.42 (9H, s), 7.7 (2H, m), 8.7 (2H, m)

Preparation 4

A mixture of N-hydroxyphthalimide (58.2 g), 1-chloro-2-cyclopentene (36.9 g), triethylamine (53.9 g) in acetonitrile (370 ml) was stirred to give N-(2-cyclopenten-1-yloxy)phthalimide (56.5 g)

IR (Nujol): 1780, 1730, 1610 cm$^{-1}$
NMR (DMSO-d$_6$, δ): 7.92 (4H, s), 6.28 (1H, m), 6.00 (1H, m), 5.42 (1H, m), 2.9–1.98 (4H, m)

Preparation 5

(1) A mixture of N-(2-cyclopenten-1-yloxy)phthalimide (22.9 g) and hydrazine hydrate (4.75 g) in ethanol (115 ml) was refluxed for 5 minutes. The reaction mixture was filtered. The filtrate containing (2-cyclopenten-1-yl)oxyamine was added to a solution of sodium 2-(5-formamido-1,2,4-thiadiazol-3-yl)glyoxylate (22.4 g) in water. The mixture was adjusted to pH 2 with 10% hydrochloric acid, stirred for 2 hours and then concentrated. The concentrate was adjusted to pH 1 with 10% hydrochloric acid. The precipitates were collected by filtration and dried to give 2-(2-cyclopenten-1-yl)oxyimino-2-(5-formamido-1,2,4-thiadiazol-3-yl)acetic acid (syn isomer) (20.0 g), mp 150° C. (dec.).

IR (Nujol): 3400, 3100, 1720, 1690, 1540 cm$^{-1}$
NMR (DMSO-d$_6$, δ): 1.80–2.50 (4H, m), 5.30–5.50 (1H, m), 5.83–6.30 (2H, m), 8.90 (1H, s)

(2) To a solution of sodium hydroxide (11.2 g) in water (140 ml) was added S-methyl 2-(5-formamido-1,2,4-thiadiazol-3-yl)thioglyoxylate (27 g) at 10° C. and the mixture was stirred for 30 minutes at 20° C. The reaction mixture containing sodium 2-(5-formamido-1,2,4-thiadiazol-3-yl)glyoxylate was cooled, adjusted to pH 7 with 10% hydrochloric acid and thereto was added a solution of cyclopentyloxyamine (15.3 g) in ethanol (150 ml). The mixture was adjusted to pH 3 with 10% hydrochloric acid, and stirred for 1.5 hours. The reaction mixture was adjusted to pH 7 with an aqueous solution of sodium bicarbonate and then evaporated to remove ethanol. The residue was washed with ethyl acetate. To the aqueous layer was added ethyl acetate and the mixture was adjusted to pH 1 with 10% hydrochloric acid. The precipitates were collected by filtration to give 2-cyclopentyloxyimino-2-(5-formamido-1,2,4-thiadiazol-3-yl)acetic acid (syn isomer) (3.99 g). The filtrate was extracted with ethyl acetate and the extract was dried over magnesium sulfate and then concentrated. The precipitates were collected by filtration and washed with diethyl ether to give the same object compound (8.1 g). Total yield: 12.09 g, mp 180° to 185° C. (dec.).

IR (Nujol): 3130, 3040, 2680, 2610, 2520, 1720, 1690, 1660, 1600, 1550 cm$^{-1}$
NMR (DMSO-d$_6$, δ): 1.33–2.10 (8H, m), 4.67–5.0 (1H, m), 8.88 (1H, s), 13.50 (1H, s)

Preparation 6

A mixture of 2-(2-cyclopenten-1-yl)oxyimino-2-(5-formamido-1,2,4-thiadiazol-3-yl)acetic acid (syn isomer) (20.0 g) and 1N aqueous solution of sodium hydroxide (200 ml) was stirred for an hour at 50° to 55° C. The reaction mixture was cooled, adjusted to pH 7 with 10% hydrochloric acid and thereto was added ethyl acetate. The mixture was adjusted to pH 1 with 10% hydrochloric acid and extracted with ethyl acetate. The extract was washed with a saturated aqueous solution of sodium chloride, dried over magnesium sulfate and evaporated. The residue was pulverized with diisopropyl ether to give 2-(2-cyclopenten-1-yl)oxyimino-2-(5-amino-1,2,4-thiadiazol-3-yl)acetic acid (syn isomer), mp 150° C. (dec.).

IR (Nujol): 3300, 3150, 1710, 1620, 1520 cm$^{-1}$
NMR (DMSO-d$_6$, δ): 1.80–2.50 (4H, m), 5.30–5.50 (1H, m), 5.83–6.30 (2H, m), 8.20 (2H, s)

Preparation 7

The following compound was obtained according to a similar manner to that of Preparation 6.
2-Cyclopentyloxyimino-2-(5-amino-1,2,4-thiadiazol-3-yl)acetic acid (syn isomer), mp 160° to 165° C. (dec.).

IR (Nujol): 3470, 3290, 3200, 2400, 1715, 1615, 1600, 1520 cm$^{-1}$
NMR (DMSO-d$_6$, δ): 1.17–2.10 (8H, m), 4.60–4.97 (1H, m), 8.22 (2H, s)

Preparation 8

A mixture of S-methyl(5-formamido-1,2,4-thiadiazol-3-yl)thioglyoxylate (6 g) and an aqueous solution (50 ml) of sodium hydroxide (4.2 g) was stirred for an hour at 50° to 55° C. The mixture was cooled to ambient temperature and adjusted to pH 7 with 10% hydrochloric acid. On the other hand, a mixture of N-(ethoxycarbonylmethoxy)phthalimide (12.9 g) and hydrazine hydrate (2.08 g) in ethanol (60 ml) was refluxed for 5 minutes and cooled in an ice bath. A resulting precipitate was filtered off and washed with ethanol. The filtrate and the washings were combined and the combined solution containing O-(ethoxycarbonylmethyl)-hydroxylamine was added to the above aqueous solution. The solution was adjusted to pH 3 to 4 with 10% hydrochloric acid and stirred for 1.5 hours at ambient temperature. The solution was neutralized with an aqueous solution of sodium bicarbonate, concentrated to half volume in vacuo and washed with ethyl acetate. The aqueous solution was acidified with 10% hydrochloric acid and extracted with ethyl acetate. The extract was dried over magnesium sulfate, evaporated to dryness and the residue was triturated with diisopropyl ether to give 2-ethoxycarbonylmethoxyimino-2-(5- amino-1,2,4-thiadiazol-3-yl)acetic acid (syn isomer) (1.8 g), mp 135° to 140° C. (dec.).

IR (Nujol): 3500, 3330, 3210, 2670, 2550, 1740, 1610, 1540 cm$^{-1}$

NMR (DMSO-d$_6$, δ): 1.24 (3H, t, J=7 Hz), 4.14 (2H, q, J=7 Hz), 4.80 (2H, s), 8.15 (2H, broad s)

Preparation 9

The following compounds were obtained according to a similar manner to that of Preparation 8.

(1) 2-(t-Butoxycarbonylmethoxyimino)-2-(5-amino-1,2,4-thiadiazol-3-yl)acetic acid (syn isomer), mp 150° to 155° C. (dec.).

IR (Nujol): 3420, 3230, 3100, 1725, 1610, 1530 cm$^{-1}$

NMR (DMSO-d$_6$, δ): 1.45 (9H, s), 4.70 (2H, s), 8.12 (2H, broad s)

(2) 2-(1-Ethoxycarbonyl-1-methylethoxyimino)-2-(5-amino-1,2,4-thiadiazol-3-yl)acetic acid (syn isomer), mp 165° to 168° C. (dec.).

IR (Nujol): 3450, 3350, 3240, 1750, 1730, 1630, 1530 cm$^{-1}$

NMR (DMSO-d$_6$, δ): 1.18 (3H, t, J=7 Hz), 1.50 (6H, s), 4.15 (2H, q, J=7 Hz), 8.23 (2H, broad s)

Preparation 10

To a cold solution of phosphorus pentachloride (16.6 g) in methylene chloride (150 ml) was added 2-ethoxyimino-2-(5-amino-1,2,4-thiadiazol-3-yl)acetic acid (syn isomer)(17.3 g) at −18° C. and the mixture was stirred for 15 minutes at −13° to −10° C. On the other hand, a mixture of 7-amino-3-acetoacetoxymethyl-3-cephem-4-carboxylic acid (25.1 g) and trimethylsilylacetamide (80 g) in methylene chloride (400 ml) was warmed to make a clear solution and cooled to −10° C. The cold solution was added to the above activated mixture and the mixture was stirred for 1 hour at −10° C. The reaction mixture was poured into an aqueous solution (450 ml) of sodium bicarbonate (42 g) and stirred for 1 hour at room temperature. The aqueous layer was separated out, adjusted to pH 2 with 6N hydrochloric acid and extracted with ethyl acetate. The extract was washed with water, dried over anhydrous magnesium sulfate and evaporated to dryness. The residue was triturated with diethyl ether to give a powder of 7-[2-ethoxyimino-2-(5-amino-1,2,4-thiadiazol-3-yl)acetamido]-3-acetoacetoxymethyl-3-cephem-4-carboxylic acid (syn isomer)(24.5 g). This compound was dissolved in 1N methanol solution of sodium acetate (48 ml) and stood on to give precipitates. Thereto was added acetone (100 ml). The precipitates were collected by filtration, washed with acetone to give sodium 7-[2-ethoxyimino-2-(5-amino-1,2,4-thiadiazol-3-yl)acetamido]-3-acetoacetoxymethyl-3-cephem-4-carboxylate (syn isomer) (19 g).

Physical constants of 7-[2-ethoxyimino-2-(5-amino-1,2,4-thiadiazol-3-yl)acetamido]-3-acetoacetoxymethyl-3-cephem-4-carboxylic acid (syn isomer): mp 101° to 106° C. (dec.).

IR (Nujol): 3400, 3300, 3170, 1770, 1710, 1660, 1620, 1525, 1145, 1035 cm$^{-1}$ Physical constants of sodium 7-[2-ethoxyimino-2-(5-amino-1,2,4-thiadiazol-3-yl)acetamido]-3-acetoacetoxymethyl-3-cephem-4-carboxylate (syn isomer): mp 175° to 180° C. (dec.).

IR (Nujol): 3450, 3300, 3100, 1790, 1720, 1670, 1640, 1610, 1550 cm$^{-1}$

NMR (D$_2$O, δ): 1.38 (3H, t, J=6 Hz), 2.34 (3H, s), 3.44, 3.66 (2H, ABq, J=18 Hz), 4.40 (2H, q, J=6 Hz), 5.05, 5.86 (2H, ABq, J=12 Hz), 5.26 (1H, d, J=4 Hz), 5.90 (1H, d, J=4 Hz)

Preparation 11

The following compounds were obtained according to a similar manner to that of Preparation 10.

(1) 7-[2-Cyclopentyloxyimino-2-(5-amino-1,2,4-thiadiazol-3-yl)acetamido]-3-acetoacetoxymethyl-3-cephem-4-carboxylic acid (syn isomer), powder, mp. 130° to 135° C. (dec.).

IR (Nujol): 3300, 1780, 1720, 1680, 1620, 1525 cm$^{-1}$

NMR (DMSO-d$_6$, δ): 1.3–2.0 (8H, m), 2.15 (3H, s), 3.52 (2H, bs), 3.60 (2H, s), 4.5–4.7 (1H, m), 4.77, 5.00 (2H, ABq, J=14 Hz), 5.13 (1H, d, J=4 Hz), 5.80 (1H, 2d, J=4 and 8 Hz), 8.10 (2H, s), 9.50 (1H, d, J=8 Hz)

(2) 7-[2-(2-Cyclopenten-1-yloxyimino)-2-(5-amino-1,2,4-thiadiazol-3-yl)acetamido]-3-acetoacetoxymethyl-3-cephem-4-carboxylic acid (syn isomer), mp. 135° to 140° C. (dec.).

IR (Nujol): 3400, 3300, 3200, 1775, 1735, 1710, 1675, 1620, 1525 cm$^{-1}$

NMR (DMSO-d$_6$, δ): 1.93–2.47 (4H, m), 2.18 (3H, s), 3.55 (2H, bs), 3.65 (2H, s), 4.80, 5.07 (2H, ABq, J=13 Hz), 5.13 (1H, d, J=5 Hz), 5.23–5.53 (1H, m), 5.70–6.23 (3H, m), 8.12 (2H, bs), 9.50 (1H, d, J=8 Hz)

(3) 7-[2-Carboxymethoxyimino-2-(5-amino-1,2,4-thiadiazol-3-yl)acetamido]-3-acetoacetoxymethyl-3-cephem-4-carboxylic acid (syn isomer), mp. 95° to 100° C. (dec.).

IR (Nujol): 3400, 3290, 3190, 1770, 1720, 1615, 1520 cm$^{-1}$

NMR (DMSO-d$_6$, δ): 2.17 (3H, s), 3.53 (2H, bs), 3.63 (2H, s), 4.67 (2H, s), 4.80, 5.07 (2H, ABq, J=13 Hz), 5.15 (1H, d, J=5 Hz), 5.87 (1H, 2d, J=5 and 8 Hz) 8.15 (2H, bs), 9.53 (1H, d, J=8 Hz)

(4) 7-[2-t-Butoxycarbonylmethoxyimino-2-(5-amino-1,2,4-thiadiazol-3-yl)acetamido]-3-acetoacetoxymethyl-3-cephem-4-carboxylic acid (syn isomer), mp. 105° to 110° C. (dec.).

IR (Nujol): 3350, 3250, 1780, 1720, 1620, 1525 cm$^{-1}$

NMR (DMSO-d$_6$, δ): 1.43 (9H, s), 2.17 (3H, s), 3.53 (2H, bs), 3.63 (2H, s), 4.63 (2H, s), 4.82, 5.05 (2H, ABq, J=13 Hz), 5.15 (1H, d, J=5 Hz), 5.85 (1H, 2d, J=5 and 8 Hz), 8.15 (2H, bs), 9.53 (1H, d, J=8 Hz)

(5) 7-[2-Cyclopentyloxyimino-2-(5-amino-1,2,4-thiadiazol-3-yl)acetamido]cephalosporanic acid (syn isomer). mp 140° to 145° C. (dec.).

IR (Nujol): 3480, 3370, 3250, 1785, 1730, 1680, 1630, 1530 cm$^{-1}$

NMR (DMSO-d$_6$, δ): 1.33–2.17 (8H, m), 2.03 (3H, s), 3.57 (2H, broad s), 4.60–4.90 (1H, m), 4.73 and 4.97 (2H, ABq, J=13 Hz), 5.15 (1H, d, J=5 Hz), 5.80 (1H, dd, J=5 and 8 Hz), 8.10 (2H, broad s), 9.47 (1H, d, J=8 Hz)

(6) 7-[2-(2-Cyclopenten-1-yl)oxyimino-2-(5-amino-1,2,4-thiadiazol-3-yl)acetamido]cephalosporanic acid (syn isomer). mp 154° to 159° C. (dec.).

IR (Nujol): 3300, 1770, 1720, 1670, 1620, 1520 cm$^{-1}$

NMR (DMSO-d$_6$, δ): 2.0 (3H, s), 2.0–2.40 (4H, m), 3.52 (2H, broad s), 4.70 and 4.97 (2H, ABq, J=14 Hz), 5.12 (1H, d, J=4 Hz), 5.27–5.40 (1H, m), 5.82 (1H, dd, J=4 and 8 Hz), 5.83–6.17 (2H, m), 8.13 (2H, s), 9.50 (1H, d, J=8 Hz)

(7) 7-[2-(t-Butoxycarbonylmethoxyimino)-2-(5-amino-1,2,4-thiadiazol-3-yl)acetamido]cephalosporanic acid (syn isomer), mp 125° to 130° C. (dec.).

IR (Nujol): 3300, 3200, 1770, 1720, 1680, 1620, 1520 cm$^{-1}$

NMR (DMSO-d$_6$, δ): 1.50 (9H, s), 2.10 (3H, s), 3.62 (2H, broad s), 4.68 (2H, s), 4.77 and 5.03 (2H, ABq, J=13 Hz), 5.20 (1H, d, J=4 Hz), 5.88 (1H, dd, J=4 and 8 Hz), 8.18 (2H, s), 9.55 (1H, d, J=8 Hz)

(8) 7-[2-Carboxymethoxyimino-2-(5-amino-1,2,4-thiadiazol-3-yl)acetamido]cephalosporanic acid (syn isomer), mp 160° to 165° C. (dec.).

IR (Nujol): 3300, 3200, 1770, 1720, 1680, 1520 cm$^{-1}$

NMR (DMSO-d$_6$, δ): 2.10 (3H, s), 3.60 (2H, broad s), 4.70 (2H, s), 4.77 and 5.03 (2H, ABq, J=14 Hz), 5.20 (1H, d, J=4 Hz), 5.88 (1H, dd, J=4 and 8 Hz), 8.18 (2H, s), 9.57 (1H, d, J=8 Hz)

Preparation 12

To a suspension of 7-(2-thienyl)acetamido-3-(3-hydroxymethyl-1-pyridiniomethyl)-3-cephem-4-carboxylate (27.0 g) and N,N-dimethylaniline (50.8 g) in methylene chloride (240 ml) was dropped trimethylsilyl chloride (26.0 g) under stirring and the mixture was stirred for 1.5 hours at room temperature. To the resulting solution was added phosphorous pentachloride (31.2 g) at −30° C. and the mixture was stirred for one hour at −30° C. to −25° C. The mixture was added to a solution of n-butanol (120 g) in methylene chloride (240 ml) at −25° C. under stirring, and the stirring was continued for 1.5 hours at room temperature. A resulting precipitate was collected by filtration, washed with methylene chloride and dried on phosphorous pentoxide to give 7-amino-3-(3-hydroxymethyl-1-pyridiniomethyl)-3-cephem-4-carboxylate dihydrochloride (25.5 g), mp 120° to 125° C. (dec.).

IR (Nujol): 1780, 1700, 1630 cm$^{-1}$

NMR (DCl+D$_2$O, δ): 3.60, 3.83 (2H, ABq, J=18 Hz), 4.97 (2H, s), 5.33 (1H, d, J=5 Hz), 5.47 (1H, d, J=5 Hz), 5.60, 5.93 (2H, ABq, J=14 Hz), 8.0-8.33 (1H, m), 8.50-8.76 (1H, m), 8.83-9.16 (2H, m)

added sodium 7-[2-ethoxyimino-2-(5-amino-1,2,4-thiadiazol-3-yl)acetamido]-cephalosporanate (syn isomer) (60 g) by portions at 75° C. under stirring, which was continued for 3 hrs. at 80° to 85° C. The mixture was cooled to 20° C. and diluted with isopropyl alcohol (3 l) to give an oily substance, which was separated by decantation. The separated oily substance was triturated in isopropyl alcohol (1 l) to give a crude object compound as a powder. The crude product was dissolved in water (500 ml) and subjected to column chromatography on a non ionic adsorption resin "Diaion HP-20" (Trademark, prepared by Mitsubishi Chemical Industries) (1.8 l). After the Column was washed with water (5.5 l), the elution was carried out with 30% aqueous methanol. The eluates (2.5 l) containing an object compound were collected, concentrated to 550 ml under reduced pressure and passed through a column packed with acidic alumina (150 g). The eluate (700 ml) was lyophilized to give white powder of 7-[2-ethoxyimino-2-(5-amino-1,2,4-thiadiazol-3-yl)acetamido]-3-(3-hydroxymethyl-1-pyridiniomethyl)-3-cephem-4-carboxylate (syn isomer) (12.5 g), mp 160° to 165° C. (dec.).

I.R. (Nujol): 3300, 1770, 1660, 1610, 1520 cm$^{-1}$

N.M.R. (D$_2$O, δ): 1.23 (3H, t, J=7 Hz), 3.23 and 3.57 (2H, ABq, J=17 Hz), 4.30 (2H, q, J=7 Hz), 4.83 (2H, s), 5.23 (1H, d, J=4 Hz), 5.33 and 5.53 (2H, ABq, J=14 Hz), 5.85 (1H, d, J=4 Hz), 8.03 (1H, dd, J=6 and 8 Hz), 8.50 (1H, d, J=8 Hz), 8.85 (1H, d, J=6 Hz), 8.90 (1H, s)

EXAMPLE 2

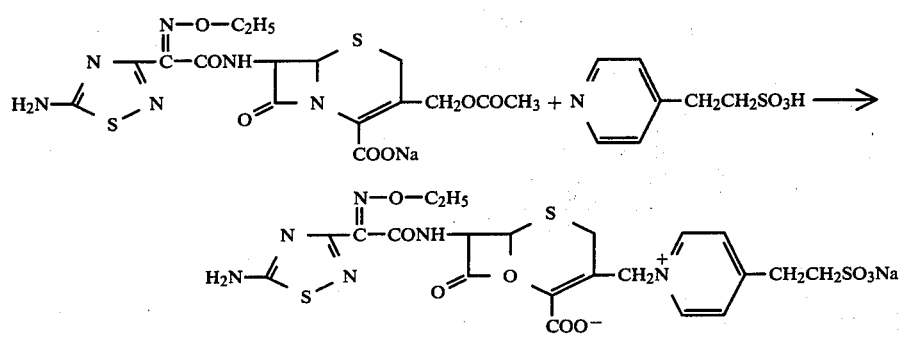

To a mixture of 4-(2-sulfoethyl)pyridine (4.56 g), potassium thiocyanate (24 g) and sodium carbonate (1.3 g) in water (25 ml) was added sodium 7-[2-ethoxyimino-2-(5-amino-1,2,4-thiadiazol-3-yl)acetamido]-cephalos-

EXAMPLE 1

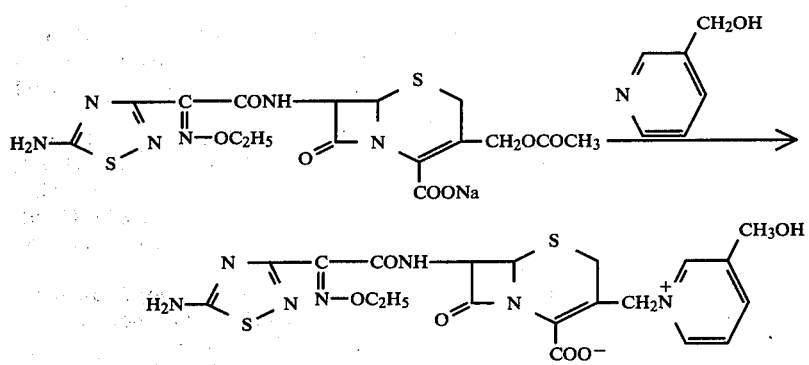

To a mixture of 3-hydroxymethylpyridine (26.6 g) and sodium iodide (150 g) in formamide (240 ml) was poranate (syn isomer) (6.0 g) at 50° C. under stirring. The mixture was stirred for 4.5 hours at 60° to 65° C., diluted with cold water and adjusted to pH 3 with 1N-hydrochloric acid. The solution was washed with ethyl acetate, evaporated to remove ethyl acetate and subjected to column chromatography on a non ionic adsorption resin "Diaion HP-20" (Trademark: Prepared by Mitsubishi Chemical Industries) (450 ml). After the column was washed with water, the elution was carried out with 20% aqueous methanol. The eluates containing an object compound were collected, evaporated to remove methanol under reduced pressure and lyophilized to give sodium 7-[2-ethoxyimino-2-(5-amino-1,2,4-thiadiazol-3-yl)acetamido]-3-[4-(2-sulfonatoethyl)-1-pyridiniomethyl]-3-cephem-4-carboxylate (syn isomer) (2.3 g), mp 165° to 171° C. (dec.).

I.R. (Nujol): 3500–3200, 1765, 1660, 1630, 1610, 1520 cm$^{-1}$

N.M.R. (D$_2$O, δ): 1.32 (3H, t, J=7 Hz), 3.16 and 3.69 (2H, ABq, J=19 Hz), 3.37 (4H, s), 4.34 (2H, q, J=7 Hz), 5.27 (1H, d, J=5 Hz), 5.28 and 5.57 (2H, ABq, J=13 Hz), 5.84 (1H, d, J=5 Hz), 7.97 (2H, d, J=7 Hz), 8.81 (2H, d, J=7 Hz)

EXAMPLE 3

To a mixture of 3-hydroxypyridine (2.32 g) and sodium iodide (15 g) in formamide (15 ml) was added sodium 7-[2-ethoxyimino-2-(5-amino-1,2,4-thiadiazol-3-yl)acetamido]cephalosporanate (syn isomer) (6.0 g) at 75° C. under stirring, which was continued for 2.5 hours at 80° to 82° C. The mixture was cooled to room temperature and poured into isopropyl alcohol (150 ml). The resulting precipitates were collected by filtration, washed with isopropyl alcohol and diisopropyl ether and then dissolved in water (80 ml). The aqueous solution was adjusted to pH 3 with 6N-hydrochloric acid, washed with ethyl acetate, evaporated to remove ethyl acetate and subjected to column chromatography on a non ionic adsorption resin "Diaion HP-20" (160 ml). After the column was washed with water, the elution was carried out with 30% aqueous methanol. The eluates containing an object compound were collected, evaporated to remove methanol under reduced pressure and lyophilized to give 7-[2-ethoxyimino-2-(5-amino-1,2,4-thiadiazol-3-yl)acetamido]-3-(3-hydroxy-1-pyridiniomethyl)-3-cephem-4-carboxylate (syn isomer) (0.93 g), mp 175° to 180° C. (dec.).

IR (Nujol): 3390, 3290, 3180, 3050, 1770, 1660, 1625, 1610, 1525 cm$^{-1}$

NMR (DMSO-d$_6$+D$_2$O, δ): 1.20 (3H, t, J=7 Hz), 3.17 and 3.47 (2H, ABq, J=18 Hz), 4.13 (2H, q, J=7 Hz), 5.07 (1H, d, J=5 Hz), 5.22 and 5.52 (2H, ABq, J=14 Hz), 5.70 (1H, d, J=5 Hz), (7.67–8.17 (2H, m), 8.40–8.90 (2H, m)

EXAMPLE 4

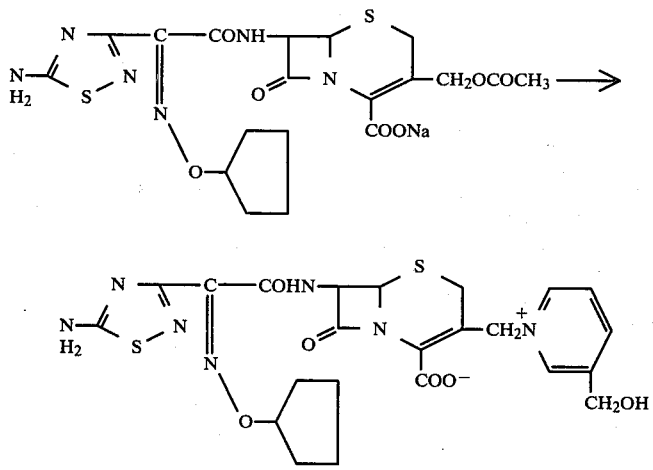

A mixture of 3-hydroxymethylpyridine (1.3 g) and potassium iodide (7.95 g) in water (5.3 ml) was warmed to 60° C. under stirring and sodium 7-[2-cyclopentyloxyimino-2-(5-amino-1,2,4-thiadiazol-3-yl)acetamido]-cephalosporanate (syn isomer) (5.32 g) was added thereto. The mixture was stirred for 5 hours at 60° C. and diluted with a mixture of water (100 ml), ethyl acetate (50 ml) and acetone (10 ml). The mixture was adjusted to pH 1 with 6N hydrochloric acid and the aqueous layer was separated out. The aqueous solution was evaporated to remove acetone and ethyl acetate and subjected to column chromatography on a non ionic adsorption resin "Diaion HP-20" (160 ml). After the column was washed with water (500 ml), the elution was carried out with 40% aqueous methanol. The eluates containing an object compound were collected, evaporated to remove methanol under reduced pressure and lyophilized to give 7-[2-cyclopentyloxyimino-2-(5-amino-1,2,4-thiadiazol-3-yl)acetamido]-3-(3-hydroxymethyl-1-pyridiniomethyl)-3-cephem-4-carboxylate (syn isomer) (1.2 g), white powder, mp 160° to 165° C. (dec.).

IR (Nujol): 3260, 3170, 1770, 1655, 1610, 1520 cm$^{-1}$

NMR (DMSO-d$_6$, δ): 1.33–2.00 (8H, m), 3.17, 3.50 (2H, ABq, J=18 Hz), 4.57–4.90 (3H, m), 5.08 (1H, d, J=5 Hz), 5.30, 5.65 (2H, ABq, J=14 Hz), 5.70 (1H, 2d, J=5 and 8 Hz), 8.00–8.33 (3H, m), 8.33–8.67 (1H, m), 9.17–9.43 (2H, m), 9.42 (1H, d, J=8 Hz)

EXAMPLE 5

To a mixture of thiazole (2.5 ml), sodium iodide (18.0 g) and water 3 ml was added sodium 7-[2-ethoxyimino-2-(5-amino-1,2,4-thiadiazol-3-yl)acetamido]-cephalosporanate (syn isomer) (5.41 g) at 60° C. under stirring, which was continued for one hour at 75° C. The reaction mixture was diluted with water (50 ml), adjusted to pH 3.6 with 1N hydrochloric acid and filtered. The filtrate was subjected to column chromatography on a non ionic adsorption resin "Diaion HP-20" (150 ml).

After the column was washed with water, the elution was carried out with 20% aqueous methanol. The eluants containing an object compound were collected, evaporated to remove methanol under reduced pressure and lyophilized to give 7-[2-ethoxyimino-2-(5-amino-1,2,4-thiadiazol-3-yl)acetamido]-3-(3-thiazoliomethyl)-3-cephem-4-carboxylate (syn isomer) (2.3 g), mp 155° to 160° C. (dec.).

IR (Nujol): 3400–3200, 1770, 1660, 1600, 1520 cm$^{-1}$

NMR (D$_2$O, δ): 1.30 (3H, t, J=7 Hz), 3.20 and 3.72 (2H, ABq, J=18 Hz), 4.32 (2H, q, J=7 Hz), 5.25 (1H, d, J=5 Hz), 5.29 and 5.50 (2H, ABq, J=13 Hz), 5.83 (1H, d, J=5 Hz), 8.19 (1H, d, J=4 Hz), 8.42 (1H, d, J=4 Hz)

EXAMPLE 6

A mixture of sodium iodide (13 g), dodecyl isonicotinate (5.8 g), 7-[2-ethoxyimino-2-(5-amino-1,2,4-thiadiazol-3-yl)acetamido]-3-acetoacetoxymethyl-3-cephem-4-carboxylic acid (syn isomer) (5.12 g), water (2.6 ml) and acetonitrile (7.8 ml) was stirred at 50° to 60° C. for 2 hours. To the reaction mixture was added a mixture of ethyl acetate (60 ml) and water (60 ml). A resulting precipitate was filtered and dissolved in a mixed solvent (1:1) of chloroform and ethanol. The solution was washed with water, dried over magnesium sulfate and concentrated to 30 ml. The resulting precipitates were filtered, washed with ethyl acetate and dried to give 7-[2-ethoxyimino-2-(5-amino-1,2,4-thiadiazol-3-yl)acetamido]-3-(4-dodecyloxycarbonyl-1-pyridiniomethyl)-3-cephem-4-carboxylate (syn isomer) (2.2 g), mp 152° to 157° C. (dec.).

IR (Nujol): 3280, 3160, 1775, 1730, 1675, 1610, 1520 cm$^{-1}$

NMR (DMSO-d$_6$+D$_2$O, δ): 0.86 (3H, t, J=6 Hz), 1.0–1.9 (23H, m), 3.22 and 3.58 (2H, ABq, J=18 Hz), 3.9–4.5 (4H, m), 5.12 (1H, d, J=5 Hz), 5.10 and 5.76 (2H, ABq, J=14 Hz), 5.72 (1H, d, J=5 Hz), 8.52 (2H, d, J=6 Hz), 9.56 (2H, d, J=6 Hz)

EXAMPLE 7

The following compound was obtained by reacting sodium 7-[2-ethoxyimino-2-(5-amino-1,2,4-thiadiazol-3-yl)acetamido]-3-acetoacetoxymethyl-3-cephem-4-carboxylate (syn isomer) with 4-cyanopyridine according to similar manners to those of Examples 1 to 6.

7-[2-Ethoxyimino-2-(5-amino-1,2,4-thiadiazol-3-yl)acetamido]-3-(4-cyano-1-pyridiniomethyl)-3-cephem-4-carboxylate (syn isomer), mp 147° to 151° C. (dec.).

IR (Nujol): 3400–3100, 1780, 1670, 1610, 1530, 1040 cm$^{-1}$

NMR (D$_2$O, δ): 1.31 (3H, t, J=7 Hz), 3.20 and 3.70 (2H, ABq, J=18 Hz), 4.31 (2H, q, J=7 Hz), 5.25 (1H, d, J=5 Hz), 5.40 and 5.71 (2H, ABq, J=14 Hz), 5.82 (1H, d, J=5 Hz), 8.45 (2H, d, J=6 Hz), 9.26 (2H, d, J=6 Hz)

EXAMPLE 8

The following compounds were obtained according to similar manners to those of Examples 1 to 7.

(1) 7-[2-Ethoxyimino-2-(5-amino-1,2,4-thiadiazol-3-yl)acetamido]-3-(4-hydroxymethyl-1-pyridiniomethyl)-3-cephem-4-carboxylate (syn isomer), mp 150° to 155° C. (dec.).

IR (Nujol): 3250, 1770, 1660, 1630, 1605, 1570, 1520 cm$^{-1}$

NMR (DMSO-d$_6$+D$_2$O, δ): 1.23 (3H, t, J=7 Hz), 3.22 and 3.58 (2H, ABq, J=18 Hz), 4.25 (2H, q, J=7 Hz), 4.90 (2H, s), 5.17 (1H, d, J=5 Hz), 5.28 and 5.65 (2H, ABq, J=14 Hz), 5.80 (1H, d, J=5 Hz), 8.12 (2H, d, J=6 Hz), 9.28 (2H, d, J=6 Hz)

(2) 7-[2-Ethoxyimino-2-(5-amino-1,2,4-thiadiazol-3-yl)acetamido]-3-(4-carboxy-1-pyridiniomethyl)-3-cephem-4-carboxylate (syn isomer), mp 175° to 185° C. (dec.).

IR (Nujol): 3400–3150, 1780, 1670, 1630, 1560, 1530, 1040 cm$^{-1}$

NMR (D$_2$O, δ): 1.22 (3H, t, J=7 Hz), 3.23 and 3.63 (2H, ABq, J=18 Hz), 4.13 (2H, q, J=7 Hz), 5.12 (1H, d, J=5 Hz), 5.33 and 5.65 (2H, ABq, J=14 Hz), 5.80 (1H, d, J=5 Hz), 8.28 (2H, d, J=6 Hz), 9.13 (2H, d, J=6 Hz)

(3) 7-[2-Ethoxyimino-2-(5-amino-1,2,4-thiadiazol-3-yl)acetamido]-3-[4-(3-hydroxypropyl)-1-pyridiniomethyl]-3-cephem-4-carboxylate (syn isomer), mp 159° to 167° C. (dec.).

IR (Nujol): 3400–3100, 1770, 1670–1610, 1540 cm$^{-1}$

NMR (DMSO-d$_6$+D$_2$O, δ): 1.23 (3H, t, J=7 Hz), 1.7–2.1 (2H, m), 2.8–3.3 (2H, m), 3.2–4.0 (4H, m), 4.20 (2H, q, J=7 Hz), 5.05 (1H, d, J=5 Hz), 5.13 and 5.63 (2H, ABq, J=14 Hz), 5.75 (1H, d, J=5 Hz), 8.02 (2H, d, J=7 Hz), 9.17 (2H, d, J=7 Hz)

(4) 7-[2-Ethoxyimino-2-(5-amino-1,2,4-thiadiazol-3-yl)acetamido]-3-(3-chloro-1-pyridiniomethyl)-3-cephem-4-carboxylate (syn isomer), mp 210° to 220° C. (dec.).

IR (Nujol): 3400–3100, 1770, 1660, 1610, 1520 cm$^{-1}$

NMR (DMSO-d$_6$+D$_2$O, δ): 1.23 (3H, t, J=7 Hz), 3.17 and 3.50 (2H, ABq, J=18 Hz), 4.15 (2H, q, J=7 Hz), 5.08 (1H, d, J=5 Hz), 5.0–5.8 (2H, m), 5.73 (1H, d, J=5 Hz), 7.8–8.8 (2H, m), 9.4 (1H, m), 9.7 (1H, m)

(5) 7-[2-Ethoxyimino-2-(5-amino-1,2,4-thiadiazol-3-yl)acetamido]-3-(3-methyl-1-pyridiniomethyl)-3-cephem-4-carboxylate (syn isomer), mp 175° to 180° C. (dec.).

IR (Nujol): 3280, 1770, 1660, 1610, 1530, 1035 cm$^{-1}$

NMR (D$_2$O, δ): 1.26 (3H, t, J=7 Hz), 2.50 (3H, s), 3.12 and 3.75 (2H, ABq, J=18 Hz), 4.29 (2H, q, J=7 Hz), 5.22 (1H, d, J=5 Hz), 5.20 and 5.53 (2H, ABq, J=13 Hz), 5.82 (1H, d, J=5 Hz), 7.88 (1H, m), 8.35 (1H, m), 8.73 (2H, m)

(6) 7-[2-Ethoxyimino-2-(5-amino-1,2,4-thiadiazol-3-yl)acetamido]-3-(3,5-dimethyl-1-pyridiniomethyl)-3-cephem-4-carboxylate (syn isomer), mp 165° to 175° C. (dec.).

IR (Nujol): 3400–3150, 1770, 1660, 1610, 1530 cm$^{-1}$

NMR (D$_2$O, δ): 1.32 (3H, t, J=7 Hz), 2.50 (6H, s), 3.21 and 3.62 (2H, ABq, J=18 Hz), 4.32 (2H, q, J=7 Hz), 4.87 (1H, d, J=5 Hz), 5.0–5.6 (3H, m), 8.16 (1H, bs), 8.58 (2H, s)

(7) 7-[2-Ethoxyimino-2-(5-amino-1,2,4-thiadiazol-3-yl)acetamido]-3-(4-t-butoxycarbonylaminomethyl-1-pyridiniomethyl)-3-cephem-4-carboxylate (syn isomer), mp 154° to 158° C. (dec.).

IR (Nujol): 3600, 1775, 1670, 1640, 1610, 1520, 1280, 1035 cm$^{-1}$

NMR (D$_2$O, δ): 1.21 (3H, t, J=7 Hz), 1.40 (9H, s), 3.0–3.7 (2H, m), 4.13 (2H, q, J=7 Hz), 4.40 (2H, broad s), 5.03 (1H, d, J=5 Hz), 4.9–5.8 (2H, m), 5.67 (1H, d, J=5 Hz), 7.90 (2H, d, J=6 Hz), 9.25 (2H, d, J=6 Hz)

(8) 7-[2-Ethoxyimino-2-(5-amino-1,2,4-thiadiazol-3-yl)acetamido]-3-(4-aminomethyl-1-pyridiniomethyl)-3-cephem-4-carboxylate diformate (syn isomer), mp 149° to 159° C. (dec.). IR (Nujol): 3250, 3150, 1770, 1660, 1640, 1580, 1520, 1040 cm$^{-1}$ (9) 7-[2-Ethoxyimino-2-(5-amino-1,2,4-thiadiazol-3-yl)acetamido]-3-(4-t-butyl-1-pyridiniomethyl)-3-cephem-4-carboxylate (syn isomer), mp 169.5° to 175.0° C. (dec.).

IR (Nujol): 3280, 1770, 1670, 1630, 1610, 1530 cm$^{-1}$

NMR (D$_2$O, δ): 1.40 (9H, s), 1.88 (3H, t, J=7 Hz), 3.13 and 3.70 (2H, ABq, J=19 Hz), 4.21 (2H, q, J=7 Hz), 5.25 and 5.56 (2H, ABq, J=14 Hz), 5.28 (1H, d, J=5 Hz), 5.87 (1H, d, J=5 Hz), 8.05 (2H, d, J=7 Hz), 8.82 (2H, d, J=7 Hz)

(10) 7-[2-Cyclopentyloxyimino-2-(5-amino-1,2,4-thiadiazol-3-yl)acetamido]-3-(4-hydroxymethyl-1-pyridiniomethyl)-3-cephem-4-carboxylate (syn isomer), mp 155° to 160° C. (dec.).

IR (Nujol): 3350, 3200, 1775, 1670, 1615, 1525 cm$^{-1}$

NMR (DMSO-d$_6$, δ): 1.20–2.00 (8H, m), 3.13, 3.50 (2H, ABq, J=18 Hz), 4.57–4.98 (3H, m), 5.08 (1H, d, J=5 Hz), 5.25, 5.60 (2H, ABq, J=14 Hz), 5.67 (1H, 2d, J=5 and 8 Hz), 8.05 (2H, d, J=6 Hz), 8.10 (2H, bs), 9.27 (2H, d, J=6 Hz), 9.40 (1H, d, J=8 Hz)

(11) 7-[2-Cyclopentyloxyimino-2-(5-amino-1,2,4-thiadiazol-3-yl)acetamido]-3-(4-acetyl-1-pyridiniomethyl)-3-cephem-4-carboxylate (syn isomer), mp 145° to 150° C. (dec.).

IR (Nujol): 3270, 1770, 1700, 1670, 1610, 1520 cm$^{-1}$

NMR (DMSO-d$_6$+D$_2$O, δ): 1.33–2.00 (8H, m), 2.67 (3H, s), 3.07, 3.45 (2H, ABq, J=18 Hz), 4.50–4.77 (1H, m), 5.02 (1H, d, J=5 Hz), 5.25, 5.58 (2H, ABq, J=14 Hz), 5.63 (1H, d, J=5 Hz), 8.40 (2H, d, J=6 Hz), 9.52 (2H, d, J=6 Hz)

(12) 7-[2-Cyclopentyloxyimino-2-(5-amino-1,2,4-thiadiazol-3-yl)acetamido]-3-(3-carboxymethyl-1-pyridiniomethyl)-3-cephem-4-carboxylate (syn isomer), mp 165° to 170° C. (dec.).

IR (Nujol): 3350, 3200, 1775, 1720, 1670, 1620, 1525 cm$^{-1}$

NMR (DMSO-d$_6$+D$_2$O, δ): 1.30–2.00 (8H, m), 3.17, 3.52 (2H, ABq, J=18 Hz), 3.93 (2H, s), 4.57–4.87 (1H, m), 5.07 (1H, d, J=5 Hz), 5.27, 5.63 (2H, ABq, J=14 Hz), 5.70 (1H, d, J=5 Hz), 7.93–8.23 (1H, m), 8.37–8.63 (1H, m), 9.10–9.37 (2H, m)

(13) 7-[2-Cyclopentyloxyimino-2-(5-amino-1,2,4-thiadiazol-3-yl)acetamido]-3-(4-hydroxyiminomethyl-1-pyridiniomethyl)-3-cephem-4-carboxylate (syn isomer), mp 140° to 145° C. (dec.).

IR (Nujol): 3280, 3160, 1770, 1680, 1630, 1610, 1520 cm$^{-1}$

NMR (DMSO-d$_6$, δ): 1.33–2.00 (8H, m), 3.23, 3.57 (2H, ABq, J=18 Hz), 4.57–4.90 (1H, m), 5.12 (1H, d, J=5 Hz), 5.28, 5.65 (2H, ABq, J=14 Hz), 5.73 (1H, 2d, J=5 and 8 Hz), 8.18 (2H, bs), 8.25 (2H, d, J=6 Hz), 8.42 (1H, s), 9.35 (2H, d, J=6 Hz), 9.43 (1H, d, J=8 Hz)

(14) 7-[2-Cyclopentyloxyimino-2-(5-amino-1,2,4-thiadiazol-3-yl)acetamido]-3-[4-methyl-5-(2-hydroxyethyl)-3-thiazoliomethyl]-3-cephem-4-carboxylate (syn isomer), mp 150° to 155° C. (dec.).

IR (Nujol): 3330, 1780, 1670, 1610, 1530 cm$^{-1}$

NMR (DMSO-d$_6$, δ): 1.33–2.00 (8H, m), 2.57 (3H, s), 2.90–3.17 (2H, m), 3.17–3.43 (2H, m), 3.57–3.80 (2H, m), 4.60–4.90 (1H, m), 5.07 (1H, d, J=5 Hz), 5.37 (2H,bs), 5.70 (1H, 2d, J=5 and 8 Hz), 8.17 (2H, bs), 9.43 (1H, d, J=8 Hz), 10.23 (1H, s)

(15) 7-[2-(2-Cyclopenten-1-yloxyimino)-2-(5-amino-1,2,4-thiadiazol-3-yl)acetamido]-3-(4-hydroxymethyl-1-pyridiniomethyl)-3-cephem-4-carboxylate (syn isomer), mp 140° to 145° C. (dec.).

IR (Nujol): 3300, 3200, 1770, 1660, 1620, 1520 cm$^{-1}$

NMR (DMSO-d$_6$, δ): 1.8–2.5 (4H, m), 3.13, 3.50 (2H, ABq, J=18 Hz), 4.83 (2H, s), 5.07 (1H, d, J=4 Hz), 5.20–5.40 (1H, m), 5.27, 5.67 (2H, ABq, J=14 Hz), 5.80 (1H, 2d, J=4 and 8 Hz), 5.87–6.20 (2H, m), 8.07 (2H, d, J=7 Hz), 8.17 (2H, s), 9.33 (2H, d, J=7 Hz), 9.47 (1H, d, J=8 Hz)

(16) 7-[2-(2-Cyclopenten-1-yloxyimino)-2-(5-amino-1,2,4-thiadiazol-3-yl)acetamido]-3-(3-hydroxymethyl-1-pyridiniomethyl)-3-cephem-4-carboxylate (syn isomer), mp 143° to 148° C. (dec.).

IR (Nujol): 3300, 3200, 1770, 1660, 1610, 1520 cm$^{-1}$

NMR (DMSO-d$_6$, δ): 1.8–2.5 (4H, m), 3.13, 3.47 (2H, ABq, J=17 Hz), 4.73 (2H, s), 5.35 (1H, d, J=4 Hz), 5.17–5.40 (1H, m), 5.40–6.20 (5H, m), 8.13 (2H, s), 8.0–8.30 (1H, m), 8.37–8.60 (1H, m), 9.27–9.43 (2H, m), 9.47 (1H, d, J=8 Hz)

(17) 7-[2-Carboxymethoxyimino-2-(5-amino-1,2,4-thiadiazol-3-yl)acetamido]-3-(3-hydroxymethyl-1-pyridiniomethyl)-3-cephem-4-carboxylate (syn isomer), mp 170° to 175° C. (dec.).

IR (Nujol): 3300, 1770, 1670, 1620, 1525 cm$^{-1}$

NMR (DMSO-d$_6$+D$_2$O, δ): 3.20, 3.50 (2H, ABq, J=18 Hz), 4.63 (2H, s), 4.73 (2H, s), 5.07 (1H, d, J=4 Hz), 5.27, 5.60 (2H, ABq, J=14 Hz), 5.87 (1H, d, J=4 Hz), 7.90–8.17 (1H, m), 8.37–8.60 (1H, m), 9.0–9.3 (2H, m)

(18) 7-[2-Ethoxycarbonylmethoxyimino-2-(5-amino-1,2,4-thiadiazol-3-yl)acetamido]-3-(3-hydroxymethyl-1-pyridiniomethyl)-3-cephem-4-carboxylate (syn isomer), mp 155° to 160° C. (dec.).

IR (Nujol): 3400–3150, 1770, 1670, 1610 cm$^{-1}$

NMR (DMSO-d$_6$+D$_2$O, δ): 1.23 (3H, t, J=7 Hz), 3.11, 3.67 (2H, ABq, J=18 Hz), 4.23 (2H, q, J=7 Hz), 4.82 (4H, bs), 5.17 (1H, d, J=5 Hz), 5.30, 5.73 (2H, ABq, J=13 Hz), 5.83 (1H, d, J=5 Hz), 8.17 (1H, m), 8.60 (1H, m), 9.23 (2H, m)

(19) 7-[2-t-Butoxycarbonylmethoxyimino-2-(5-amino-1,2,4-thiadiazol-3-yl)acetamido]-3-(3-hydroxymethyl-1-pyridiniomethyl)-3-cephem-4-carboxylate (syn isomer), mp 145° to 150° C. (dec.).

IR (Nujol): 3300, 1775, 1740, 1670, 1610, 1525 cm$^{-1}$

NMR (DMSO-d$_6$+D$_2$O, δ): 1.50 (9H, s), 3.23, 3.60 (2H, Abq, J=17 Hz), 4.65 (2H, s), 4.80 (2H, s), 5.13 (1H, d, J=4 Hz), 5.37, 5.67 (2H, ABq, J=14 Hz), 5.80 (1H, d, J=4 Hz), 8.23 (2H, s), 8.0–8.27 (1H, m), 8.43–8.67 (1H, m), 9.30–9.50 (2H, m),

(20) 7-[2-(1-Methyl-1-ethoxycarbonylethoxyimino)-2-(5-amino-1,2,4-thiadiazol-3-yl)acetamido]-3-(3-hydroxymethyl-1-pyridiniomethyl)-3-cephem-4-carboxylate (syn isomer), mp 155° to 160° C. (dec.).

IR (Nujol): 3400–3200, 1780, 1740, 1680 cm$^{-1}$

NMR (DMSO-d$_6$+D$_2$O, δ): 1.16 (3H, t, J=7 Hz), 1.48 (6H, s), 3.16, 3.62 (2H, ABq, J=18 Hz), 4.16 (2H, q, J=7 Hz), 4.80 (2H, s), 5.14 (1H, d, J=5 Hz), 5.2–5.8 (2H, m), 5.80 (1H, d, J=5 Hz), 8.20 (1H, m), 8.56 (1H, m), 9.32 (2H, m)

(21) 7-[2-Ethoxyimino-2-(5-amino-1,2,4-thiadiazol-3-yl)acetamido]-3-[4-(N-hydroxycarbamoyl)-1-pyridiniomethyl]-3-cephem-4-carboxylate (syn isomer), mp 178° to 185° C. (dec.).

IR (Nujol): 3250, 3180, 1770, 1670, 1640, 1605, 1530 cm$^{-1}$

NMR (D$_2$O, δ): 1.29 (3H, t, J=7 Hz), 3.20 and 3.72 (2H, ABq, J=19 Hz), 4.30 (2H, q, J=7 Hz), 5.28 (1H, d, J=5 Hz), 5.37 and 5.70 (2H, ABq, J=14 Hz), 5.88 (1H, d, J=5 Hz), 8.31 (2H, d, J=7 Hz), 9.13 (2H, d, J=7 Hz)

(22) 7-[2-Ethoxyimino-2-(5amino-1,2,4-thiadiazol-3-yl)acetamido]-3-(4-butoxycarbonyl-1-pyridiniomethyl)-3-cephem-4-carboxylate (syn isomer), mp 154° to 159° C. (dec.).

IR (Nujol): 3300, 3160, 1775, 1728, 1670, 1605, 1525 cm$^{-1}$

NMR (DMSO-d$_6$+D$_2$O, δ): 0.8–2.0 (10H, m), 3.13 and 3.53 (2H, ABq, J=18 Hz), 4.0–4.6 (4H, m), 5.08 (1H, d, J=5 Hz), 5.33 and 5.76 (2H, ABq, J=14 Hz), 5.73 (1H, d, J=5 Hz), 8.55 (2H, d, J=6 Hz), 9.72 (2H, d, J=6 Hz)

(23) 7-[2-Ethoxyimino-2-(5-amino-1,2,4-thiadiazol-3-yl)acetamido]-3-(4-t-butoxycarbonyl-1-pyridiniomethyl)-3-cephem-4-carboxylate (syn isomer), mp 154° to 157° C. (dec.).

IR (Nujol): 3300, 3150, 1775, 1725, 1670, 1610, 1525 cm$^{-1}$

NMR (DMSO-d$_6$+D$_2$O, δ): 1.23 (3H, t, J=6.5 Hz), 1.60 (9H, s), 3.25 and 3.63 (2H, ABq, J=18 Hz), 4.17 (2H, q, J=6.5 Hz), 5.10 (1H, d, J=5 Hz), 5.30 and 5.83 (2H, ABq, J=14 Hz), 5.72 (1H, d, J=5 Hz), 8.52 (2H, d, J=6 Hz), 9.68 (2H, d, J=6 Hz)

(24) 7-[2-Ethoxyimino-2-(5-amino-1,2,4-thiadiazol-3-yl)acetamido]-3-[4-(N-butylcarbamoyl)-1-pyridiniomethyl]-3-cephem-4-carboxylate (syn isomer), mp 161° to 162° C. (dec.).

IR (Nujol): 3270, 1775, 1655, 1610, 1560, 1530 cm$^{-1}$

NMR (DMSO-d$_6$, δ): 0.90 (3H, t, J=7 Hz), 1.20 (3H, t, J=7 Hz), 1.1-1.8 (4H, m), 2.9-3.9 (4H, m), 4.15 (2H, q, J=7 Hz), 5.08 1 (1H, d, J=5 Hz), 5.28 and 5.73 (2H, ABq, J=14 Hz), 5.72 (1H, 2d, J=5 and 8 Hz), 8.15 (2H, bs), 8.53 (2H, d, J=6 Hz), 9.48 (1H, d, J=8 Hz), 9.60 (2H, d, J=6 Hz)

(25) 7-[2-Ethoxyimino-2-(5-amino-1,2,4-thiadiazol-3-yl)acetamido]-3-[4-(N-t-butylcarbamoyl)-1-pyridiniomethyl]-3-cephem-4-carboxylate (syn isomer), mp 165° to 167° C. (dec.).

IR (Nujol): 3270, 1775, 1660, 1610, 1530 cm$^{-1}$

NMR (DMSO-d$_6$+D$_2$O, δ): 1.22 (3H, t, J=7 Hz), 1.42 (9H, s), 3.16 and 3.50 (2H, ABq, J=18 Hz), 4.17 (2H, q, J=7 Hz), 5.08 (1H, d, J=5 Hz), 5.25 and 5.68 (2H, ABq, J=14 Hz), 5.72 (1H, d, J=5 Hz), 8.47 (2H, d, J=7 Hz), 9.62 (2H, d, J=7 Hz)

(26) 7-[2-Ethoxyimino-2-(5-amino-1,2,4-thiadiazol-3-yl)acetamido]-3-[4-(N-dodecylcarbamoyl)-1-pyridiniomethyl]-3-cephem-4-carboxylate (syn isomer), mp 176° to 177° C. (dec.).

IR (Nujol): 3270, 1770, 1655, 1610, 1540 cm$^{-1}$

NMR (DMSO-d$_6$+D$_2$O, δ): 0.85 (3H, t, J=5 Hz), 1.0-1.8 (23H, m), 3.18 and 3.57 (2H, ABq, J=18 Hz), 3.1-3.9 (2H, m), 4.15 (2H, q, J=7 Hz), 5.0-6.0 (4H, m), 8.6 (2H, bs), 9.6 (2H, bs)

(27) 7-[2-Ethoxyimino-2-(5-amino-1,2,4-thiadiazol-3-yl)acetamido]-3-(4-octyloxycarbonyl-1-pyridiniomethyl)-3-cephem-4-carboxylate (syn isomer), mp 155° to 158° C. (dec.).

IR (Nujol): 3270, 1775, 1735, 1680, 1615, 1520 cm$^{-1}$

NMR (DMSO-d$_6$+D$_2$O, δ): 0.86 (3H, t, J=6 Hz), 1.0-1.7 (15H, m), 3.25 and 3.53 (2H, ABq, J=18 Hz), 3.9-4.7 (4H, m), 5.15 (1H, d, J=5 Hz), 5.50 and 5.72 (2H, ABq, J=14 Hz), 5.83 (1H, d, J=5 Hz), 8.57 (2H, d, J=6 Hz), 9.62 (2H, d, J=6 Hz)

(28) 7-[2-Ethoxyimino-2-(5-amino-1,2,4-thiadiazol-3-yl)acetamido]-3-[4-(N-octylcarbamoyl)-1-pyridiniomethyl]-3-cephem-4-carboxylate (syn isomer), mp 181° to 183° C. (dec.).

IR (Nujol): 3250, 1770, 1655, 1610, 1565, 1550, 1530 cm$^{-1}$

NMR (DMSO-d$_6$+D$_2$O, δ): 0.86 (3H, t, J=6 Hz), 0.9-1.7 (15H, m), 2.9-3.6 (4H, m), 4.15 (2H, q, J=6 Hz), 5.15 (1H, d, J=5 Hz), 5.15 and 5.77 (2H, ABq, J=14 Hz), 5.77 (1H, d, J=5 Hz), 8.62 (2H, d, J=6 Hz), 9.51 (2H, d, J=6 Hz)

(29) 7-[2-Ethoxyimino-2-(5-amino-1,2,4-thiadiazol-3-yl)acetamido]-3-(3-mesylamino-1-pyridiniomethyl)-3-cephem-4-carboxylate (syn isomer), mp 170° to 175° C. (dec.).

IR (Nujol): 3400, 1760, 1670, 1610, 1520, 1150 cm$^{-1}$

NMR (DMSO-d$_6$, δ): 1.17 (3H, t, J=7 Hz), 2.87 (3H, s), 3.20 and 3.47 (2H, ABq, J=16 Hz), 4.10 (2H, q, J=7 Hz), 5.10 (1H, d, J=4 Hz), 5.17 and 5.47 (2H, ABq, J=14 Hz), 5.80 (1H, 2d, J=4 and 8 Hz), 7.6-8.5 (4H, m), 9.47 (1H, d, J=8 Hz)

(30) 7-[2-Ethoxyimino-2-(5-amino-1,2,4-thiadiazol-3-yl)acetamido]-3-(4-ethoxycarbonyl-1-pyridiniomethyl)-3-cephem-4-carboxylate (syn isomer), mp 150° to 155° C. (dec.).

IR (Nujol): 3320, 3160, 1775, 1730, 1670, 1610, 1530, 1290 cm$^{-1}$

NMR (DMSO-d$_6$+D$_2$O, δ): 1.21 (3H, t, J=7 Hz), 1.36 (3H, t, J=7 Hz), 3.12, 3.52 (2H, Abq, J=18 Hz), 4.12 (2H, q, J=7 Hz), 4.43 (2H, q, J=7 Hz), 5.06 (1H, d, J=5 Hz), 5.33, 5.68 (2H, ABq, J=14 Hz), 5.71 (1H, d, J=5 Hz), 8.47 (2H, d, J=6 Hz), 9.60 (2H, d, J=6 Hz)

EXAMPLE 8

A solution of 7-[2-ethoxyimino-2-(5-amino-1,2,4-thiadiazol-3-yl)acetamido]-3-(4-t-butoxycarbonylaminomethyl-1-pyridiniomethyl)-3-cephem-4-carboxylate (syn isomer) (1.23 g) in formic acid (20 ml) was stirred for 6.5 hours at ambient temperature. The solution was evaporated to dryness under reduced pressure and the residue was dissolved in water. An insoluble material was filtered off and the filtrate was subjected to column chromatography on a non-ionic adsorption resin "Diaion HP-20" (50 ml). The elution was carried out with water. The eluates containing an object compound were collected and lyophilized to give 7-[2-ethoxyimino-2-(5-amino-1,2,4-thiadiazol-3-yl)acetamido]-3-(4-aminomethyl-1-pyridiniomethyl)-3-cephem-4-carboxylate diformate (syn isomer) (0.37 g), mp 149° to 159° C. (dec.).

IR (Nujol): 3250, 3150, 1770, 1660, 1640, 1580, 1520, 1040 cm$^{-1}$

NMR (D$_2$O, δ): 1.22 (3H, t, J=7 Hz), 3.3-3.9 (2H, m), 4.05 (2H, broad s), 4.17 (2H, q, J=7 Hz), 4.9-5.6 (2H, m), 5.06 (1H, d, J=4 Hz), 5.70 (1H, d, J=4 Hz), 7.45 (2H, d, J=5 Hz), 8.26 (2H, s), 8.55 (2H, d, J=5 Hz)

EXAMPLE 10

To a cold solution of phosphorus pentachloride (3.2 g) in methylene chloride (45 ml) was added 2-t-butoxycarbonylmethoxyimino-2-(5-amino-1,2,4-thiadiazol-3-yl)acetic acid (syn isomer) (4.2 g) at −18° C. and the mixture was stirred for 45 minutes at −12° to −10° C. To the reaction mixture was added diisopropyl ether (150 ml) at −10° C. and the mixture was stirred for several minutes and the resulting precipitate was collected by filtration. On the other hand, a mixture of 7-amino-3-(3-hydroxymethyl-1-pyridiniomethyl)-3-cephem-4-carboxylate dihydrochloride (4.0 g) and trimethylsilylacetamide (20 g) in methylene chloride (40 ml) was stirred for 30 minutes at room temperature and cooled to −20° C. To the cold solution was added the precipitate obtained above and the mixture was stirred for 30 minutes at −10° to −5° C. The reaction mixture was poured into an aqueous solution (100 ml) of sodium bicarbonate (5.9 g) and stirred for 30 minutes at room temperature. The aqueous layer was separated out. To the aqueous solution was added ethyl acetate and the mixture was adjusted to pH 1.5 with 6 N hydrochloric acid. The aqueous layer was separated out, washed with ethyl acetate and subjected to column chromatography on a non ionic adsorption resin "Diaion HP-20" (100 ml). After the column was washed with water. The elution was carried out with 40% aqueous methanol.

The eluates containing an object compound were collected, evaporated to remove methanol under reduced pressure and lyophilized to give 7-[2-t-butoxycarbonylmethoxyimino-2-(5-amino-1,2,4-thiadiazol-3-yl)acetamido]-3-(3-hydroxymethyl-1-pyridiniomethyl)-3-cephem-4-carboxylate (syn isomer) (2.2 g), mp 145° to 150° C. (dec.).

IR (Nujol): 3300, 1775, 1740, 1670, 1610, 1525 cm$^{-1}$

NMR (DMSO-$d_6$+$D_2O$, δ): 1.50 (9H, s), 3.23, 3.60 (2H, ABq, J=17 Hz), 4.65 (2H, s), 4.80 (2H, s), 5.13 (1H, d, J=4 Hz), 5.37, 5.67 (2H, ABq, J=14 Hz), 5.80 (1H, d, J=4 Hz), 8.23 (2H, s), 8.0–8.27 (1H, m), 8.43–8.67 (1H, m), 9.30–9.50 (2H, m).

EXAMPLE 11

The following compounds were obtained according to a similar manner to that of Example 10.

(1) 7-[2-Ethoxyimino-2-(5-amino-1,2,4-thiadiazol-3-yl)acetamido]-3-(3-hydroxymethyl-1-pyridiniomethyl)-3-cephem-4-carboxylate (syn isomer), mp 160° to 165° C. (dec.).

IR (Nujol): 3300, 1770, 1660, 1610, 1520 cm$^{-1}$ (2) Sodium 7-[2-ethoxyimino-2-(5-amino-1,2,4-thiadiazol-3-yl)acetamido]-3-[4-(2-sulfonatoethyl)-1-pyridiniomethyl]-3-cephem-4-carboxylate (syn isomer), mp 165° to 171° C. (dec.).

IR (Nujol): 3500–3200, 1765, 1660, 1630, 1610, 1520 cm$^{-1}$ (3) 7-[2-Ethoxyimino-2-(5-amino-1,2,4-thiadiazol-3-yl)acetamido]-3-(3-hydroxy-1-pyridiniomethyl)-3-cephem-4-carboxylate (syn isomer), mp 175° to 180° C. (dec.).

IR (Nujol): 3390, 3290, 3180, 3050, 1770, 1660, 1625, 1610, 1525 cm$^{-1}$ (4) 7-[2-Ethoxyimino-2-(5-amino-1,2,4-thiadiazol-3-yl)acetamido]-3-(4-cyano-1-pyridiniomethyl)-3-cephem-4-carboxylate (syn isomer), mp 147° to 151° C. (dec.).

IR (Nujol): 3400–3100, 1780, 1670, 1610, 1530, 1040 cm$^{-1}$ (5) 7-[2-Ethoxyimino-2-(5-amino-1,2,4-thiadiazol-3-yl)acetamido]-3-(4-hydroxymethyl-1-pyridiniomethyl)-3-cephem-4-carboxylate (syn isomer), mp 150° to 155° C. (dec.).

IR (Nujol): 3250, 1770, 1660, 1630, 1605, 1570, 1520 cm$^{-1}$ (6) 7-[2-Ethoxyimino-2-(5-amino-1,2,4-thiadiazol-3-yl)acetamido]-3-(4-carboxy-1-pyridiniomethyl)-3-cephem-4-carboxylate (syn isomer), mp 175° to 185° C. (dec.).

IR (Nujol): 3400–3150, 1780, 1670, 1630, 1560, 1530, 1040 cm$^{-1}$ (7) 7-[2-Ethoxyimino-2-(5-amino-1,2,4-thiadiazol-3-yl)acetamido]-3-[4-(3-hydroxypropyl)-1-pyridiniomethyl]-3-cephem-4-carboxylate (syn isomer), mp 159° to 167° C. (dec.).

IR (Nujol): 3400–3100, 1770, 1670–1610, 1540 cm$^{-1}$ (8) 7-[2-Ethoxyimino-2-(5-amino-1,2,4-thiadiazol-3-yl)acetamido]-3-(3-chloro-1-pyridiniomethyl)-3-cephem-4-carboxylate (syn isomer), mp 210° to 220° C. (dec.).

IR (Nujol): 3400–3100, 1770, 1660, 1610, 1520 cm$^{-1}$ (9) 7-[2-Ethoxyimino-2-(5-amino-1,2,4-thiadiazol-3-yl)acetamido]-3-(3-methyl-1-pyridiniomethyl)-3-cephem-4-carboxylate (syn isomer), mp 175° to 180° C. (dec.).

IR (Nujol): 3280, 1770, 1660, 1610, 1530, 1035 cm$^{-1}$

(10) 7-[2-Ethoxyimino-2-(5-amino-1,2,4-thiadiazol-3-yl)acetamido]-3-(3,5-dimethyl-1-pyridiniomethyl)-3-cephem-4-carboxylate (syn isomer), mp 165° to 175° C. (dec.).

IR (Nujol): 3400–3150, 1770, 1660, 1610, 1530 cm$^{-1}$

(11) 7-[2-Ethoxyimino-2-(5-amino-1,2,4-thiadiazol-3-yl)acetamido]-3-(4-t-butoxycarbonylaminomethyl-1-pyridiniomethyl)-3-cephem-4-carboxylate (syn isomer), mp 154° to 158° C. (dec.).

IR (Nujol): 3600, 1775, 1670, 1640, 1610, 1520, 1280, 1035 cm$^{-1}$

(12) 7-[2-Ethoxyimino-2-(5-amino-1,2,4-thiadiazol-3-yl)acetamido]-3-(4-aminomethyl-1-pyridiniomethyl)-3-cephem-4-carboxylate diformate (syn isomer), mp 149° to 159° C. (dec.).

IR (Nujol): 3250, 3150, 1770, 1660, 1640, 1580, 1520, 1040 cm$^{-1}$

(13) 7-[2-Ethoxyimino-2-(5-amino-1,2,4-thiadiazol-3-yl)acetamido]-3-(4-t-butyl-1-pyridiniomethyl)-3-cephem-4-carboxylate (syn isomer), mp 169.5° to 175.0° C. (dec.).

IR (Nujol): 3280, 1770, 1670, 1630, 1610, 1530 cm$^{-1}$

(14) 7-[2-Cyclopentyloxyimino-2-(5-amino-1,2,4-thiadiazol-3-yl)acetamido]-3-(4-hydroxymethyl-1-pyridiniomethyl)-3-cephem-4-carboxylate (syn isomer), mp 155° to 160° C. (dec.).

IR (Nujol): 3350, 3200, 1775, 1670, 1615, 1525 cm$^{-1}$

(15) 7-[2-Cyclopentyloxyimino-2-(5-amino-1,2,4-thiadiazol-3-yl)acetamido]-3-(3-hydroxymethyl-1-pyridiniomethyl)-3-cephem-4-carboxylate (syn isomer), mp 160° to 165° C. (dec.).

IR (Nujol): 3260, 3170, 1770, 1655, 1610, 1520 cm$^{-1}$

(16) 7-[2-Cyclopentyloxyimino-2-(5-amino-1,2,4-thiadiazol-3-yl)acetamido]-3-(4-acetyl-1-pyridiniomethyl)-3-cephem-4-carboxylate (syn isomer), mp 145° to 150° C. (dec.).

IR (Nujol): 3270, 1770, 1700, 1670, 1610, 1520 cm$^{-1}$

(17) 7-[2-Cyclopentyloxyimino-2-(5-amino-1,2,4-thiadiazol-3-yl)acetamido]-3-(3-carboxymethyl-1-pyridiniomethyl)-3-cephem-4-carboxylate (syn isomer), mp 165° to 170° C. (dec.).

IR (Nujol): 3350, 3200, 1775, 1720, 1670, 1620, 1525 cm$^{-1}$

(18) 7-[2-Cyclopentyloxyimino-2-(5-amino-1,2,4-thiadiazol-3-yl)acetamido]-3-(4-hydroxyiminomethyl-1-pyridiniomethyl)-3-cephem-4-carboxylate (syn isomer), mp 140° to 145° C. (dec.).

IR (Nujol): 3280, 3160, 1770, 1680, 1630, 1610, 1520 cm$^{-1}$

(19) 7-[2-Cyclopentyloxyimino-2-(5-amino-1,2,4-thiadiazol-3-yl)acetamido]-3-[4-methyl-5-(2-hydroxyethyl)-3-thiazoliomethyl]-3-cephem-4-carboxylate (syn isomer), mp 150° to 155° C. (dec.).

IR (Nujol): 3330, 1780, 1670, 1610, 1530 cm$^{-1}$

(20) 7-[2-(2-Cyclopenten-1-yloxyimino)-2-(5-amino-1,2,4-thiadiazol-3-yl)acetamido]-3-(4-hydroxymethyl-1-pyridiniomethyl)-3-cephem-4-carboxylate (syn isomer), mp 140° to 145° C. (dec.).

IR (Nujol): 3300, 3200, 1770, 1660, 1620, 1520 cm$^{-1}$

(21) 7-[2-(2-Cyclopenten-1-yloxyimino)-2-(5-amino-1,2,4-thiadiazol-3-yl)acetamido]-3-(3-hydroxymethyl-1-pyridiniomethyl)-3-cephem-4-carboxylate (syn isomer), mp 143° to 148° C. (dec.).

IR (Nujol): 3300, 3200, 1770, 1660, 1610, 1520 cm$^{-1}$

(22) 7-[2-Carboxymethoxyimino-2-(5-amino-1,2,4-thiadiazol-3-yl)acetamido]-3-(3-hydroxymethyl-1-pyridiniomethyl)-3-cephem-4-carboxylate (syn isomer), mp 170° to 175° C. (dec.).

IR (Nujol): 3300, 1770, 1670, 1620, 1525 cm$^{-1}$

(23) 7-[2-Ethoxycarbonylmethoxyimino-2-(5-amino-1,2,4-thiadiazol-3-yl)acetamido]-3-(3-hydroxymethyl- 1-pyridiniomethyl)-3-cephem-4-carboxylate (syn isomer), mp 155° to 160° C. (dec.).

IR (Nujol): 3400–3150, 1770, 1670, 1610 cm$^{-1}$

NMR (DMSO-$d_6$+$D_2O$, δ): 1.23 (3H, t, J=7 Hz), 3.11, 3.67 (2H, ABq, J=18 Hz), 4.23 (2H, q, J=7 Hz), 4.82 (4H, bs), 5.17 (1H, d, J=5 Hz), 5.30, 5.73 (2H, ABq, J=13 Hz), 5.83 (1H, d, J=5 Hz), 8.17 (1H, m), 8.60 (1H, m), 9.23 (2H, m)

(24) 7-[2-Ethoxyimino-2-(5-amino-1,2,4-thiadiazol-3-yl)acetamido]-3-(3-mesylamino-1-pyridiniomethyl)-3-cephem-4-carboxylate (syn isomer), mp 170° to 175° C. (dec.).

IR (Nujol): 3400, 1760, 1670, 1610, 1520, 1150 cm$^{-1}$

(25) 7-[2-(1-Methyl-1-ethoxycarbonylethoxyimino)-2-(5-amino-1,2,4-thiadiazol-3-yl)acetamido]-3-(3-hydroxymethyl-1-pyridiniomethyl)-3-cephem-4-carboxylate (syn isomer), mp 155° to 160° C. (dec.).

IR (Nujol): 3400–3200, 1780, 1740, 1680 cm$^{-1}$

NMR (DMSO-$d_6$+$D_2O$, δ): 1.16 (3H, t, J=7 Hz), 1.48 (6H, s), 3.16, 3.62 (2H, ABq, J=18 Hz), 4.16 (2H, q, J=7 Hz), 4.80 (2H, s), 5.14 (1H, d, J=5 Hz), 5.2–5.8 (2H, m), 5.80 (1H, d, J=5 Hz), 8.20 (1H, m), 8.56 (1H, m), 9.32 (2H, m)

(26) 7-[2-Ethoxyimino-2-(5-amino-1,2,4-thiadiazol-3-yl)acetamido]-3-(3-thiazoliomethyl)-3-cephem-4-carboxylate (syn isomer), mp 155° to 160° C. (dec.).

IR (Nujol): 3400–3200, 1770, 1660, 1600, 1520 cm$^{-1}$

(27) 7-[2-Ethoxyimino-2-(5-amino-1,2,4-thiadiazol-3-yl)acetamido]-3-[4-(N-hydroxycarbamoyl)-1-pyridiniomethyl]-3-cephem-4-carboxylate (syn isomer), mp 178° to 185° C. (dec.).

IR (Nujol): 3250, 3180, 1770, 1670, 1640, 1605, 1530 cm$^{-1}$

(28) 7-[2-Ethoxyimino-2-(5-amino-1,2,4-thiadiazol-3-yl)acetamido]-3-(4-butoxycarbonyl-1-pyridiniomethyl)-3-cephem-4-carboxylate (syn isomer), mp 154° to 159° C. (dec.).

IR (Nujol): 3300, 3160, 1775, 1728, 1670, 1605, 1525 cm$^{-1}$

(28) 7-[2-Ethoxyimino-2-(5-amino-1,2,4-thiadiazol-3-yl)acetamido]-3-(4-t-butoxycarbonyl-1-pyridiniomethyl)-3-cephem-4-carboxylate (syn isomer), mp 154° to 157° C. (dec.).

IR (Nujol): 3300, 3150, 1775, 1725, 1670, 1610, 1525 cm$^{-1}$

(30) 7-[2-Ethoxyimino-2-(5-amino-1,2,4-thiadiazol-3-yl)acetamido]-3-[4-(N-butylcarbamoyl)-1-pyridiniomethyl]-3-cephem-4-carboxylate (syn isomer), mp 161° to 162° C. (dec.).

IR (Nujol): 3270, 1775, 1655, 1610, 1560, 1530 cm$^{-1}$

(31) 7-[2-Ethoxyimino-2-(5-amino-1,2,4-thiadiazol-3-yl)acetamido]-3-[4-(N-t-butylcarbamoyl)-1-pyridiniomethyl]-3-cephem-4-carboxylate (syn isomer), mp 165° to 167° C. (dec.).

IR (Nujol): 3270, 1775, 1660, 1610, 1530 cm$^{-1}$

(32) 7-[2-Ethoxyimino-2-(5-amino-1,2,4-thiadiazol-3-yl)acetamido]-3-(4-dodecyloxycarbonyl-1-pyridiniomethyl)-3-cephem-4-carboxylate (syn isomer), mp 152° to 157° C. (dec.).

IR (Nujol): 3280, 3160, 1775, 1730, 1675, 1610, 1520 cm$^{-1}$

(33) 7-[2-Ethoxyimino-2-(5-amino-1,2,4-thiadiazol-3-yl)acetamido]-3-[4-(N-dodecylcarbamoyl)-1-pyridiniomethyl]-3-cephem-4-carboxylate (syn isomer), mp 176° to 177° C. (dec.).

IR (Nujol): 3270, 1770, 1655, 1610, 1540 cm$^{-1}$

(34) 7-[2-Ethoxyimino-2-(5-amino-1,2,4-thiadiazol-3-yl)acetamido]-3-(4-octyloxycarbonyl-1-pyridiniomethyl)-3-cephem-4-carboxylate (syn isomer), mp 155° to 158° C. (dec.).

IR (Nujol): 3270, 1775, 1735, 1680, 1615, 1520 cm$^{-1}$

(35) 7-[2-Ethoxyimino-2-(5-amino-1,2,4-thiadiazol-3-yl)acetamido]-3-[4-(N-octylcarbamoyl)-1-pyridiniomethyl]-3-cephem-4-carboxylate (syn isomer), mp 181° to 183° C. (dec.).

IR (Nujol): 3250, 1770, 1655, 1610, 1565, 1550, 1530 cm$^{-1}$

(36) 7-[2-Ethoxyimino-2-(5-amino-1,2,4-thiadiazol-3-yl)acetamido]-3-(4-ethoxycarbonyl-1-pyridiniomethyl)-3-cephem-4-carboxylate (syn isomer), mp 150° to 155° C. (dec.).

IR (Nujol): 3320, 3160, 1775, 1730, 1670, 1610, 1530, 1290 cm$^{-1}$

NMR (DMSO-$d_6$+$D_2O$, δ): 1.21 (3H, t, J=7 Hz), 1.36 (3H, t, J=7 Hz), 3.12, 3.52 (2H, ABq, J=18 Hz), 4.12 (2H, q, J=7 Hz), 4.43 (2H, q, J=7 Hz), 5.06 (1H, d, J=5 Hz), 5.33, 5.68 (2H, ABq, J=14 Hz), 5.71 (1H, d, J=5 Hz), 8.47 (2H, d, J=6 Hz), 9.60 (2H, d, J=6 Hz)

EXAMPLE 12

To a cold mixture of trifluoroacetic acid (14 ml) and anisole (2.5 ml) was added 7-[2-t-butoxycarbonylmethoxyimino-2-(5-amino-1,2,4-thiadiazol-3-yl)acetamido]-3-(3-hydroxymethyl-1-pyridiniomethyl)-3-cephem-4-carboxylate (syn isomer) (2.0 g) under stirring and the mixture was stirred for 80 minutes at room temperature. The mixture was evaporated to remove trifluoroacetic acid and the residue was triturated with isopropyl alcohol to give a powder. The powder was dissolved in water. The aqueous solution was subjected to a column chromatography on a non ionic adsorption resin "Diaion HP-20" (100 ml). After the column was washed with water, the elution was carried out with 15% aqueous methanol. The eluates containing an object compound were collected, evaporated to remove methanol under reduced pressure and lyophilized to give 7-[2-carboxymethoxyimino-2-(5-amino-1,2,4-thiadiazol-3-yl)acetamido]-3-(3-hydroxymethyl-1-pyridiniomethyl)-3-cephem-4-carboxylate (syn isomer) (1.05 g), mp 170° to 175° C. (dec.).

IR (Nujol): 3300, 1770, 1670, 1620, 1525 cm$^{-1}$

NMR (DMSO-$d_6$+$D_2O$, δ): 3.20, 3.50 (2H, ABq, J=18 Hz), 4.63 (2H, s), 4.73 (2H, s), 5.07 (1H, d, J=4 Hz), 5.27, 5.60 (2H, ABq, J=14 Hz), 5.87 (1H, d, J=4 Hz), 7.90–8.17 (1H, m), 8.37–8.60 (1H, m), 9.0–9.3 (2H, m)

Preparation 13

To a solution of phosphorus pentachloride (54.6 g) in methylene chloride (500 ml) was added 2-ethoxyimino-2-(5-amino-1,2,4-thiadiazol-3-yl)acetic acid (syn isomer) (54.0 g) under stirring and cooling at −20° C. The mixture was stirred for 30 minutes at −15° to −12° C. and for 2 hours at −5° C. To the mixture containing precipitates of an object compound was added diisopropyl ether (500 ml) at −5° C. and the mixture was stirred for 30 minutes at −5° to 10° C. The resulting precipitates were collected by filtration, washed with diisopropyl ether and dried to give 2-ethoxyimino-2-(5-amino-1,2,4-thiadiazol-3-yl)acetyl chloride hydrochloride (syn isomer) (60.17 g), mp. 125° to 127° C. (dec.).

I.R. (Nujol): 1785, 1625, 1055 cm$^{-1}$

| Analysis for $C_6H_8O_2N_4SCl_2$ | | | | |
|---|---|---|---|---|
| | C | H | N | S | Cl |
| calc'd: | 26.57 | 2.95 | 20.66 | 11.81 | 26.20 |
| found: | 26.13 | 2.99 | 20.49 | 11.77 | 26.41 |

Preparation 14

To a suspension of diphenylmethyl 7-amino-3-chloromethyl-3-cephem-4-carboxylate hydrochloride (27 g) in methylene chloride (300 ml) was added N,N-dimethylaniline (36.2 g) under cooling in an ice bath at 5° C. To the solution was added portionwise 2-ethoxyimino-2-(5-amino-1,2,4-thiadiazol-3-yl)acetyl chloride hydrochloride (syn isomer) (16.2 g) below 11° C. and the mixture was stirred for 45 minutes at 5° C. The reaction mixture was diluted with a mixed solvent of methylene chloride (100 ml) and water (200 ml) and adjusted to pH 2 with 1N hydrochloric acid. The organic layer was separated out, washed with water, dried over magnesium sulfate and evaporated to dryness. The residue was triturated in diethyl ether to give diphenylmethyl 7-[2-ethoxyimino-2-(5-amino-1,2,4-thiadiazol-3-yl)acetamido]-3-chloromethyl-3-cephem-4-carboxylate (syn isomer) (32.4 g), mp. 120° to 125° C. (dec.).

I.R. (Nujol): 3300, 3150, 1780, 1725, 1675, 1625, 1530, 1495 cm$^{-1}$

N.M.R. (DMSO-$d_6$, $\delta$): 1.28 (3H, t, J=7 Hz), 3.68 (2H, broad s), 4.23 (2H, q, J=7 Hz), 4.47 (2H, s), 5.27 (1H, d, J=5 Hz), 5.97 (1H, 2d, J=5 and 8 Hz), 7.0 (1H, s), 7.2–7.7 (10H, m), 8.17 (2H, broad s), 9.62 (1H, d, J=8 Hz)

Preparation 15

To a cold solution of diphenylmethyl 7-[2-ethoxyimino-2-(5-amino-1,2,4-thiadiazol-3-yl)acetamido]-3-chloromethyl-3-cephem-4-carboxylate (syn isomer) (10 g) in a mixed solution of methylene chloride (100 ml) and acetic acid (10 ml) were added 30% hydrogen peroxide (1.84 ml) and sodium tungstate (0.3 g).

The mixture was stirred for 45 minutes in an ice bath and poured into diethyl ether (300 ml). The precipitates were collected by filtration and washed with diethyl ether to give diphenylmethyl 7-[2-ethoxyimino-2-(5-amino-1,2,4-thiadiazol-3-yl)acetamido]-3-chloromethyl-3-cephem-4-carboxylate-1-oxide (syn isomer) (8.9 g), mp 150° to 155° C. (dec.).

I.R. (Nujol): 3280, 3170, 1785, 1723, 1667, 1628, 1530 cm$^{-1}$

N.M.R. (DMSO-$d_6$, $\delta$): 1.30 (3H, t, J=7 Hz), 3.90 (2H, broad s), 4.23 (2H, q, J=7 Hz), 4.58 (2H, broad s), 5.12 (1H, d, J=5 Hz), 6.10 (1H, 2d, J=5 and 8 Hz), 7.02 (1H, s), 7.20–7.73 (10H, m), 8.15 (2H, broad s), 9.00 (1H, d, J=8 Hz)

Preparation 16

To a cold solution of diphenylmethyl 7-[2-ethoxyimino-2-(5-amino-1,2,4-thiadiazol-3-yl)acetamido]-3-chloromethyl-3-cephem-4-carboxylate-1-oxide (syn isomer) (9.85 g) in acetone (222 ml) was added sodium iodide (8.22 g) and the mixture was stirred for 2 hours under cooling in an ice bath. The solvent was evaporated under reduced pressure and the residue was dissolved in a mixture of methylene chloride (200 ml) and water (100 ml). The organic layer was separated out, washed with an aqueous solution of sodium thiosulfate and water successively, dried over magnesium sulfate and evaporated to dryness. The residue was triturated in diethyl ether to give diphenylmethyl 7-[2-ethoxyimino-2-(5-amino-1,2,4-thiadiazol-3-yl)acetamido]-3-iodomethyl-3-cephem-4-carboxylate-1-oxide (syn isomer) (10.39 g), mp. 159° to 163° C. (dec.).

I.R. (Nujol): 3250, 3150, 1780, 1720, 1670, 1620, 1520 cm$^{-1}$

N.M.R. (DMSO-$d_6$, $\delta$): 1.29 (3H, t, J=7 Hz), 3.95 (2H, m), 4.25 (2H, q, J=7 Hz), 4.50 (2H, m), 5.12 (1H, d, J=5 Hz), 6.05 (1H, 2d, J=5 and 9 Hz), 7.00 (1H, s), 7.4 (10H, m), 8.13 (2H, broad s), 8.96 (1H, d, J=9 Hz)

Preparation 17

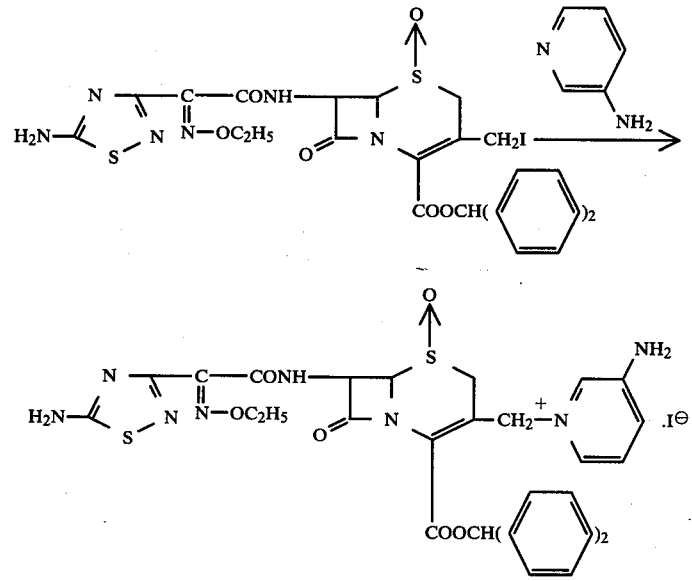

A mixture of diphenylmethyl 7-[2-ethoxyimino-2-(5-amino-1,2,4-thiadiazol-3-yl)acetamido]-3-iodomethyl-3-cephem-4-carboxylate-1-oxide (syn isomer) (5.0 g) and 3-aminopyridine (0.717 g) in tetrahydrofuran (35 ml) was stirred for one hour at room temperature. The resulting precipitates were collected by filtration, washed with tetrahydrofuran and diethyl ether and dried to give diphenylmethyl 7-[2-ethoxyimino-2-(5-amino-1,2,4-thiadiazol-3-yl)-acetamido]-3-(3-amino-1-pyridiniomethyl)-3-cephem-4-carboxylate-1-oxide iodide (syn isomer) (5.41 g), mp 157° to 162° C. (dec.).

I.R. (Nujol): 3400–3200, 1795, 1725, 1680, 1610, 1530, 1510, 1035, 705 cm$^{-1}$ N.M.R. (DMSO-d$_6$, δ): 1.26 (3H, t, J=7 Hz), 3.3–4.0 (2H, m), 4.19 (2H, q, J=7 Hz), 5.08 (1H, d, J=5 Hz), 5.35 (2H, broad s), 6.10 (1H, 2d, J=5 and 8 Hz), 6.6 (2H, m), 6.92 (1H, s), 7.1–7.7 (12H, m), 7.9 (2H, m), 8.03 (2H, broad s), 8.93 (1H, d, J=8 Hz)

Preparation 18

To a mixture of diphenylmethyl 7-[2-ethoxyimino-2-(5-amino-1,2,4-thiadiazol-3-yl)acetamido]-3-(3-amino-1-pyridiniomethyl)-3-cephem-4-carboxylate-1-oxide iodide (syn isomer) (4.50 g) and N,N-dimethylaniline (1.34 g) in acetonitrile (45 ml) was dropped phosphorus trichloride (1.52 g) below 8° C. under stirring and cooling in an ice bath. The mixture was stirred for 70 minutes at the same temperature and diethyl ether (50 ml) was added thereto. The resulting precipitates were collected by filtration, washed with diethyl ether and dried to give diphenylmethyl 7-[2-ethoxyimino-2-(5-amino-1,2,4-thiadiazol-3-yl)acetamido]-3-(3-amino-1-pyridiniomethyl)-3-cephem-4-carboxylate iodide (syn isomer) (5.05 g), mp. 85° to 95° C. (dec.).

I.R. (Nujol): 3300, 3200, 1790, 1680, 1630, 1510, 1220, 1185 cm$^{-1}$

N.M.R. (DMSO-d$_6$+D$_2$O, δ): 1.23 (3H, t, J=7 Hz), 3.2–3.8 (2H, m), 4.13 (2H, q, J=7 Hz), 5.0–5.8 (4H, m), 6.87 (1H, s), 7.1–7.8 (12H, m), 7.8–8.1 (2H, m)

Preparation 19

A solution of diphenylmethyl 7-[2-ethoxyimino-2-(5-amino-1,2,4-thiadiazol-3-yl)acetamido]-3-(3-amino-1-pyridiniomethyl)-3-cephem-4-carboxylate iodide (syn isomer) (4.9 g) in a mixed solvent (12 ml) of acetone and methanol (1:1) was subjected to a column packed with an ion-exchange resin [Amberlite IRA-400 (Trademark: prepared by Rohm & Haas Co.) trifluoroacetate-form] (50 ml). The elution was carried out with the same solvent (100 ml) and the eluate was evaporated to dryness. The residue was triturated in diethyl ether to give diphenylmethyl 7-[2-ethoxyimino-2-(5-amino-1,2,4-thiadiazol-3-yl)acetamido]-3-(3-amino-1-pyridiniomethyl)-3-cephem-4-carboxylate trifluoroacetate (syn isomer) (3.72 g), mp. 125° to 130° C. (dec.).

I.R. (Nujol): 3300, 3200, 1790, 1690–1620, 1510, 1200, 1180, 1035 cm$^{-1}$

N.M.R. (DMSO-d$_6$, δ): 1.25 (3H, t, J=7 Hz), 3.2–3.7 (2H, m), 4.19 (2H, q, J=7 Hz), 5.1–5.5 (2H, m), 5.29 (1H, d, J=5 Hz), 6.00 (1H, 2d, J=5 and 8 Hz), 6.91 (1H, s), 7.1–7.7 (12H, m), 7.8–8.3 (4H, m), 9.73 (1H, d, J=8 Hz)

EXAMPLE 13

A mixture of diphenylmethyl 7-[2-ethoxyimino-2-(5-amino-1,2,4-thiadiazol-3-yl)acetamido]-3-(3-amino-1-pyridiniomethyl)-3-cephem-4-carboxylate trifluoroacetate (syn isomer) (500 mg) and anisole (1.0 ml) in trifluoroacetic acid (2 ml) was stirred for 35 minutes under cooling in an ice-salt bath. The mixture was poured into cold diisopropyl ether (20 ml) under stirring and resulting precipitates were collected by filtration. The powder was suspended in water (18 ml), adjusted to pH 4 to 5 with aqueous solution of sodium bicarbonate and an insoluble material was filtered off. The filtrate was subjected to column chromatography on a non ionic adsorption resin "Diaion HP 20" (Trademark: Prepared by Mitsubishi Chemical Industries) (20 ml). After the column was washed with water, the elution was carried out with 20% aqueous methanol. The eluates containing an object compound were collected, evaporated to remove methanol under reduced pressure and lyophilized to give 7-[2-ethoxyimino-2-(5-amino-1,2,4-thiadiazol-3-yl)acetamido]-3-(3-amino-1-pyridiniomethyl)-3-cephem-4-carboxylate (syn isomer) (100 mg), mp. 175° to 180° C. (dec.).

I.R. (Nujol): 3300, 3200, 1770, 1660–1590, 1510, 1150, 1035 cm$^{-1}$

N.M.R. (DMSO-d$_6$, δ): 1.24 (3H, t, J=7 Hz), 3.04 and 3.53 (2H, ABq, J=18 Hz), 4.16 (2H, q, J=7 Hz), 5.06 and 5.61 (2H, ABq, J=14 Hz), 5.10 (1H, d, J=5 Hz), 5.73 (1H, 2d, J=5 and 8 Hz), 6.6–7.2 (2H, m), 7.7 (2H, m), 8.22 (2H, broad s), 8.5–8.6 (2H, m), 9.51 (1H, d, J=8 Hz)

EXAMPLE 14

The following compounds were obtained according to a similar manner to that of Example 13.

(1) 7-[2-Ethoxyimino-2-(5-amino-1,2,4-thiadiazol-3-yl)acetamido]-3-(3-hydroxymethyl-1-pyridiniomethyl)-3-cephem-4-carboxylate (syn isomer), mp. 160° to 165° C. (dec.).

I.R. (Nujol): 3300, 1770, 1660, 1610, 1520 cm$^{-1}$ (2) Sodium 7-[2-ethoxyimino-2-(5-amino-1,2,4-thiadiazol-3-yl)acetamido]-3-[4-(2-sulfonatoethyl)-1-pyridiniomethyl]-3-cephem-4-carboxylate (syn isomer), mp. 165° to 171° C. (dec.).

I.R. (Nujol): 3500–3200, 1765, 1660, 1630, 1610, 1520 cm$^{-1}$ (3) 7-[2-Ethoxyimino-2-(5-amino-1,2,4-thiadiazol-3-yl)acetamido]-3-(3-hydroxy-1-pyridiniomethyl)-3-cephem-4-carboxylate (syn isomer), mp. 175° to 180° C. (dec.).

I.R. (Nujol): 3390, 3290, 3180, 3050, 1770, 1660, 1625, 1610, 1525 cm$^{-1}$ (4) 7-[2-Ethoxyimino-2-(5-amino-1,2,4-thiadiazol-3-yl)acetamido]-3-(4-cyano-1-pyridiniomethyl)-3-cephem-4-carboxylate (syn isomer), mp. 147° to 151° C. (dec.).

I.R. (Nujol): 3400–3100, 1780, 1670, 1610, 1530, 1040 cm$^{-1}$ (5) 7-[2-Ethoxyimino-2-(5-amino-1,2,4-thiadiazol-3-yl)acetamido]-3-(4-hydroxymethyl-1-pyridiniomethyl)-3-cephem-4-carboxylate (syn isomer), mp. 150° to 155° C. (dec.).

I.R. (Nujol): 3250, 1770, 1660, 1630, 1605, 1570, 1520 cm$^{-1}$ (6) 7-[2-Ethoxyimino-2-(5-amino-1,2,4-thiadiazol-3-yl)acetamido]-3-(4-carboxy-1-pyridiniomethyl)-3-cephem-4-carboxylate (syn isomer), mp 175° to 185° C. (dec.).

I.R. (Nujol): 3400–3150, 1780, 1670, 1630, 1560, 1530, 1040 cm$^{-1}$ (7) 7-[2-Ethoxyimino-2-(5-amino-1,2,4-thiadiazol-3-yl)acetamido]-3-[4-(3-hydroxypropyl)-1-pyridiniomethyl]-3-cephem-4-carboxylate (syn isomer), mp. 159° to 167° C. (dec.).

I.R. (Nujol): 3400–3100, 1770, 1670–1610, 1540 cm$^{-1}$ (8) 7-[2-Ethoxyimino-2-(5-amino-1,2,4-thiadiazol-3-yl)acetamido]-3-(3-chloro-1-pyridiniomethyl)-3-cephem-4-carboxylate (syn isomer), mp. 210° to 220° C. (dec.).

I.R. (Nujol): 3400–3100, 1770, 1660, 1610, 1520 cm$^{-1}$ (9) 7-[2-Ethoxyimino-2-(5-amino-1,2,4-thiadiazol-3-yl)acetamido]-3-(3-methyl-1-pyridiniomethyl)-3-cephem-4-carboxylate (syn isomer), mp. 175° to 180° C. (dec.).

I.R. (Nujol): 3280, 1770, 1660, 1610, 1530, 1035 cm$^{-1}$

(10) 7-[2-Ethoxyimino-2-(5-amino-1,2,4-thiadiazol-3-yl)acetamido]-3-(3,5-dimethyl-1-pyridiniomethyl)-3-cephem-4-carboxylate (syn isomer), mp. 165° to 175° C. (dec.).
I.R. (Nujol): 3400–3150, 1770, 1660, 1610, 1530 cm$^{-1}$

(11) 7-[2-Ethoxyimino-2-(5-amino-1,2,4-thiadiazol-3-yl)acetamido]-3-(4-aminomethyl-1-pyridiniomethyl)-3-cephem-4-carboxylate diformate (syn isomer), mp. 149° to 159° C. (dec.).
I.R. (Nujol): 3250, 3150, 1770, 1660, 1640, 1580, 1520, 1040 cm$^{-1}$

(12) 7-[2-Ethoxyimino-2-(5-amino-1,2,4-thiadiazol-3-yl)acetamido]-3-(4-t-butyl-1-pyridiniomethyl)-3-cephem-4-carboxylate (syn isomer), mp. 169.5° to 175.0° C. (dec.).
I.R. (Nujol): 3280, 1770, 1670, 1630, 1610, 1530 cm$^{-1}$

(13) 7-[2-(Cyclopentyloxyimino-2-(5-amino-1,2,4-thiadiazol-3-yl)acetamido]-3-(4-hydroxymethyl-1-pyridiniomethyl)-3-cephem-4-carboxylate (syn isomer), mp. 155° to 160° C. (dec.).
I.R. (Nujol): 3350, 3200, 1775, 1670, 1615, 1525 cm$^{-1}$

(14) 7-[2-Cyclopentyloxyimino-2-(5-amino-1,2,4-thiadiazol-3-yl)acetamido]-3-(3-hydroxymethyl-1-pyridiniomethyl)-3-cephem-4-carboxylate (syn isomer), mp. 160° to 165° C. (dec.).
I.R. (Nujol): 3260, 3170, 1770, 1655, 1610, 1520 cm$^{-1}$

(15) 7-[2-Cyclopentyloxyimino-2-(5-amino-1,2,4-thiadiazol-3-yl)acetamido]-3-(4-acetyl-1-pyridiniomethyl)-3-cephem-4-carboxylate (syn isomer), mp. 145° to 150° C. (dec.).
I.R. (Nujol): 3270, 1770, 1700, 1670, 1610, 1520 cm$^{-1}$

(16) 7-[2-Cyclopentyloxyimino-2-(5-amino-1,2,4-thiadiazol-3-yl)acetamido]-3-(3-carboxymethyl-1-pyridiniomethyl)-3-cephem-4-carboxylate (syn isomer), mp. 165° to 170° C. (dec.).
I.R. (Nujol): 3350, 3200, 1775, 1720, 1670, 1620, 1525 cm$^{-1}$

(17) 7-[2-cyclopentyloxyimino-2-(5-amino-1,2,4-thiadiazol-3-yl)acetamido]-3-(4-hydroxyiminomethyl-1-pyridiniomethyl)-3-cephem-4-carboxylate (syn isomer), mp. 140° to 145° C. (dec.).
I.R. (Nujol): 3280, 3160, 1770, 1680, 1630, 1610, 1520 cm$^{-1}$

(18) 7-[2-Cyclopentyloxyimino-2-(5-amino-1,2,4-thiadiazol-3-yl)acetamido]-3-[4-methyl-5-(2-hydroxyethyl)-3-thiazoliomethyl]-3-cephem-4-carboxylate (syn isomer), mp. 150° to 155° C. (dec.).
I.R. (Nujol): 3330, 1780, 1670, 1610, 1530 cm$^{-1}$

(19) 7-[2-(2-Cyclopenten-1-yloxyimino)-2-(5-amino-1,2,4-thiadiazol-3-yl)acetamido]-3-(4-hydroxymethyl-1-pyridiniomethyl)-3-cephem-4-carboxylate (syn isomer), mp. 140° to 145° C. (dec.).
I.R. (Nujol): 3300, 3200, 1770, 1660, 1620, 1520 cm$^{-1}$

(20) 7-[2-(2-Cyclopenten-1-yloxyimino)-2-(5-amino-1,2,4-thiadiazol-3-yl)acetamido]-3-(3-hydroxymethyl-1-pyridiniomethyl)-3-cephem-4-carboxylate (syn isomer), mp. 143° to 148° C. (dec.).
I.R. (Nujol): 3300, 3200, 1770, 1660, 1610, 1520 cm$^{-1}$

(21) 7-[2-Carboxymethoxyimino-2-(5-amino-1,2,4-thiadiazol-3-yl)acetamido]-3-(3-hydroxymethyl-1-pyridiniomethyl)-3-cephem-4-carboxylate (syn isomer), mp. 170° to 175° C. (dec.).
I.R. (Nujol): 3300, 1770, 1670, 1620, 1525 cm$^{-1}$

(22) 7-[2-Ethoxycarbonylmethoxyimino-2-(5-amino-1,2,4-thiadiazol-3-yl)acetamido]-3-(3-hydroxymethyl-1-pyridiniomethyl)-3-cephem-4-carboxylate (syn isomer), mp. 155° to 160° C. (dec.).
I.R. (Nujol): 3400–3150, 1770, 1670, 1610 cm$^{-1}$

(23) 7-[2-Ethoxyimino-2-(5-amino-1,2,4-thiadiazol-3-yl)acetamido]-3-(3-mesylamino-1-pyridiniomethyl)-3-cephem-4-carboxylate (syn isomer), mp. 170° to 175° C. (dec.).
I.R. (Nujol): 3400, 1760, 1670, 1610, 1520, 1150 cm$^{-1}$

(24) 7-[2-(1-methyl-1-ethoxycarbonylethoxyimino)-2-(5-amino-1,2,4-thiadiazol-3-yl)acetamido]-3-(3-hydroxymethyl-1-pyridiniomethyl)-3-cephem-4-carboxylate (syn isomer), mp. 155° to 160° C. (dec.).
I.R. (Nujol): 3400–3200, 1780, 1740, 1680 cm$^{-1}$

(25) 7-[2-Ethoxyimino-2-(5-amino-1,2,4-thiadiazol-3-yl)acetamido]-3-(3-thiazoliomethyl)-3-cephem-4-carboxylate (syn isomer), mp. 155° to 160° C. (dec.).
I.R. (Nujol): 3400–3200, 1770, 1660, 1600, 1520 cm$^{-1}$

(26) 7-[2-Ethoxyimino-2-(5-amino-1,2,4-thiadiazol-3-yl)acetamido]-3-[4-(N-hydroxycarbamoyl)-1-pyridiniomethyl]-3-cephem-4-carboxylate (syn isomer), mp. 178° to 185° C. (dec.).
I.R. (Nujol): 3250, 3180, 1770, 1670, 1640, 1605, 1530 cm$^{-1}$

(27) 7-[2-Ethoxyimino-2-(5-amino-1,2,4-thiadiazol-3-yl)acetamido]-3-(4-butoxycarbonyl-1-pyridiniomethyl)-3-cephem-4-carboxylate (syn isomer), mp. 154° to 159° C. (dec.).
I.R. (Nujol): 3300, 3160, 1775, 1728, 1670, 1605, 1525 cm$^{-1}$

(28) 7-[2-Ethoxyimino-2-(5-amino-1,2,4-thiadiazol-3-yl)acetamido]-3-[4-(N-butylcarbamoyl)-1-pyridiniomethyl]-3-cephem-4-carboxylate (syn isomer), mp. 161° to 162° C. (dec.).
I.R. (Nujol): 3270, 1775, 1655, 1610, 1560, 1530 cm$^{-1}$

(29) 7-[2-Ethoxyimino-2-(5-amino-1,2,4-thiadiazol-3-yl)acetamido]-3-[4-(N-t-butylcarbamoyl)-1-pyridiniomethyl]-3-cephem-4-carboxylate (syn isomer), mp. 165° to 167° C. (dec.).
I.R. (Nujol): 3270, 1775, 1660, 1610, 1530 cm$^{-1}$

(30) 7-[2-Ethoxyimino-2-(5-amino-1,2,4-thiadiazol-3-yl)acetamido]-3-(4-dodecyloxycarbonyl-1-pyridiniomethyl)-3-cephem-4-carboxylate (syn isomer), mp. 152° to 157° C. (dec.).
I.R. (Nujol): 3280, 3160, 1775, 1730, 1675, 1610, 1520 cm$^{-1}$

(31) 7-[2-Ethoxyimino-2-(5-amino-1,2,4-thiadiazol-3-yl)acetamido]-3-[4-(N-dodecylcarbamoyl)-1-pyridiniomethyl]-3-cephem-4-carboxylate (syn isomer), mp. 176° to 177° C. (dec.).
I.R. (Nujol): 3270, 1770, 1655, 1610, 1540 cm$^{-1}$

(32) 7-[2-Ethoxyimino-2-(5-amino-1,2,4-thiadiazol-3-yl)acetamido]-3-(4-octyloxycarbonyl-1-pyridiniomethyl)-3-cephem-4-carboxylate (syn isomer), mp. 155° to 158° C. (dec.).
I.R. (Nujol): 3270, 1775, 1735, 1680, 1615, 1520 cm$^{-1}$

(33) 7-[2-Ethoxyimino-2-(5-amino-1,2,4-thiadiazol-3-yl)acetamido]-3-[4-(N-octylcarbamoyl)-1-pyridiniomethyl]-3-cephem-4-carboxylate (syn isomer), mp. 181° to 183° C. (dec.).
I.R. (Nujol): 3250, 1770, 1655, 1610, 1565, 1550, 1530 cm$^{-1}$

(34) 7-[2-Ethoxyimino-2-(5-amino-1,2,4-thiadiazol-3-yl)acetamido]-3-(4-ethoxycarbonyl-1-pyridiniomethyl)-3-cephem-4-carboxylate (syn isomer), mp. 150° to 155° C. (dec.).
I.R. (Nujol): 3320, 3160, 1775, 1730, 1670, 1610, 1530, 1290 cm$^{-1}$

EXAMPLE 15

The following compounds were obtained according to similar manners to those of aforesaid Examples.

(1) 7-[2-Ethoxyimino-2-(5-amino-1,2,4-thiadiazol-3-yl)acetamido]-3-(3-amino-1-pyridiniomethyl)-3-cephem-4-carboxylate (syn isomer), mp. 175° to 180° C. (dec.).

I.R. (Nujol): 3300, 3200, 1770, 1660–1590, 1510, 1150, 1035 cm$^{-1}$ (2) 7-[2-Ethoxyimino-2-(5-amino-1,2,4-thiadiazol-3-yl)acetamido]-3-(4-hexadecyloxycarbonyl-1-pyridiniomethyl)-3-cephem-4-carboxylate (syn isomer), mp. 161° to 166° C. (dec.).

I.R. (Nujol): 3400, 3250, 1770, 1730, 1670, 1610, 1520, 1285, 1120, 1035 cm$^{-1}$ N.M.R. (DMSO-d$_6$+D$_2$O, δ): 0.83 (3H, t, J=7 Hz), 1.0–1.7 (29H, m), 3.2–3.8 (2H, m), 4.0–4.5 (4H, m), 4.9–5.3 (2H, m), 5.5–6.0 (2H, m), 8.4 (2H, m), 9.4 (2H, m)

Preparation 20

The following compound was obtained according to a similar manner to that of Preparation 3. Hexadecyl isonicotinate, mp. 60° to 63° C.

I.R. (Nujol): 1722, 1560, 1480, 1410, 1290, 1275 cm$^{-1}$
N.M.R. (DMSO-d$_6$, δ): 0.7–1.8 (31H, m), 4.30 (2H, t, J=5 Hz), 7.7 (2H, m), 8.7 (2H, m)

Preparation 21

Sodium 7-[2-methoxyimino-2-(5-amino-1,2,4-thiadiazol-3-yl)acetamido]cephalosporanate (syn isomer) was obtained by reacting 7-[2-methoxyimino-2-(5-amino-1,2,4-thiadiazol-3-yl)acetamido]cephalosporanic acid (syn isomer) with sodium acetate in a conventional manner.

mp 185° to 190° C. (dec.)

I.R. (Nujol): 3150, 1765, 1745, 1670, 1550, 1400, 1355, 1290, 1250, 1055 cm$^{-1}$

EXAMPLE 16

A mixture of 3-formamidopyridine (5.1 g), sodium iodide (36 g), phosphoric acid (1.24 g), water (6 ml) and acetonitrile (18 ml) was heated at 65° to 70° C. under stirring and sodium 7-[2-methoxyimino-2-(5-amino-1,2,4-thiadiazol-3-yl)acetamido]cephalosporanate (syn isomer) (10 g) was added thereto. The mixture was stirred for 1.5 hours at 70° to 72° C. and diluted with water (50 ml). The aqueous solution was cooled, adjusted to pH 3 with 6N hydrochloric acid and diluted with water to 200 ml. The aqueous solution was washed five times with a mixed solvent (150 ml) of chloroform and ethanol (2:1) and concentrated to 300 ml under reduced pressure. An insoluble material was filtered off and the filtrate was subjected to column chromatography on a non ionic adsorption resin "Diaion HP 20" (Trademark: Prepared by Mitsubishi Chemical Industries) (300 ml). After the column was washed with water, the elution was carried out with 10% aqueous methanol. The eluates containing an object compound were collected, evaporated to remove methanol under reduced pressure and lyophilized to give 7-[2-methoxyimino-2-(5-amino-1,2,4-thiadiazol-3-yl)acetamido]-3-(3-formamido-1-pyridiniomethyl)-3-cephem-4-carboxylate (syn isomer) (5.20 g), mp. 158° to 163° C. (dec).

I.R. (nujol): 3400~3100, 1770, 1670, 1600, 1530 cm$^{-1}$

N.M.R. (D$_2$O, δ): 3.20 and 3.73 (2H, ABq, J=18 Hz), 4.03 (3H, s), 5.28 (1H, d, J=5 Hz), 5.30 and 5.67 (2H, ABq, J=14 Hz), 5.88 (1H, d, J=5 Hz), 7.9~8.2 (1H, m), 8.3~8.6 (1H, m), 8.45 (1H, s), 8.6~8.8 (1H, m), 9.5 (1H, m)

EXAMPLE 17

To a suspension of 7-[2-methoxyimino-2-(5-amino-1,2,4-thiadiazol-3-yl)acetamido]-3-(3-formamido-1-pyridiniomethyl)-3-cephem-4-carboxylate (syn isomer) (4.48 g) in methanol (45 ml) was added concentrated hydrochloric acid (1.7 ml) and the mixture was stirred for 75 minutes. The solvent was evaporated and the residue was triturated in acetone. The obtained powder was suspended in water (100 ml), adjusted to pH 4 to 5 with aqueous solution of sodium bicarbonate and subjected to column chromatography on a non ionic adsorption resin "Diaion HP 20" (Trademark: Prepared by Mitsubishi Chemical Industries) (135 ml). After the column was washed with water, the elution was carried out with 15% aqueous isopropyl alcohol. The eluates containing an object compound were collected, evaporated to remove isopropyl alcohol under reduced pressure and lyophilized to give 7-[2-methoxyimino-2-(5-amino-1,2,4-thiadiazol-3-yl)acetamido]-3-(3-amino-1-pyridiniomethyl)-3-cephem-4-carboxylate (syn isomer) (3.10 g), mp 177° to 182° C. (dec.).

I.R. (Nujol): 3350, 3200, 1770, 1640~1590, 1510 cm$^{-1}$

N.M.R. (D$_2$O, δ): 3.15 and 3.65 (2H, ABq, J=18 Hz), 4.04 (3H, s), 5.2~5.4 (2H, m), 5.23 (1H, d, J=5 Hz), 5.85 (1H, d, J=5 Hz), 7.6~7.7 (2H, m), 8.0~8.1 (1H, m), 8.2 (1H, m)

EXAMPLE 18

The following compounds were obtained according to similar manners to those of aforesaid Examples.
(1) 7-[2-Methoxyimino-2-(5-amino-1,2,4-thiadiazol-3-yl)acetamido]-3-(3-formamido-1-pyridiniomethyl)-3-cephem-4-carboxylate (syn isomer), mp 158° to 163° C. (dec.).

I.R. (Nujol): 3400~3100, 1770, 1670, 1600, 1530 cm$^{-1}$

N.M.R. (D$_2$O, δ): 3.20 and 3.73 (2H, ABq, J=18 Hz), 4.03 (3H, s), 5.28 (1H, d, J=5 Hz), 5.30 and 5.67 (2H, ABq, J=14 Hz), 5.88 (1H, d, J=5 Hz), 7.9~8.2 (1H, m), 8.3~8.6 (1H, m), 8.45 (1H, s), 8.6~8.8 (1H, m), 9.5 (1H, m)

(2) 7-[2-Methoxyimino-2-(5-amino-1,2,4-thiadiazol-3-yl)acetamido]-3-(3-amino-1-pyridiniomethyl)-3-cephem-4-carboxylate (syn isomer), mp 177° to 182° C. (dec.).

I.R. (Nujol): 3350, 3200, 1770, 1640~1590, 1510 cm$^{-1}$

N.M.R. (D$_2$O, δ): 3.15 and 3.65 (2H, ABq, J=18 Hz), 4.04 (3H, s), 5.2~5.4 (2H, m), 5.23 (1H, d, J=5 Hz), 5.85 (1H, d, J=5 Hz), 7.6~7.7 (2H, m), 8.0–8.1 (1H, m), 8.2 (1H, m)

(3) 7-[2-Ethoxyimino-2-(5-amino-1,2,4-thiadiazol-3-yl)acetamido]-3-(3-formamido-1-pyridiniomethyl)-3-cephem-4-carboxylate (syn isomer), mp 158° to 165° C. (dec.).

I.R. (Nujol): 3250, 3100, 1760, 1670, 1600, 1540 cm$^{-1}$

N.M.R. (DMSO-d$_6$+D$_2$O, δ): 1.20 (3H, t, J=7 Hz), 3.0~3.6 (2H, m), 4.18 (2H, q, J=7 Hz), 5.1~5.9 (2H, m), 5.17 (1H, d, J=5 Hz), 5.77 (1H, d, J=5 Hz), 7.9~8.2 (1H, m), 8.48 (1H, s), 8.5~8.7 (1H, m), 8.9~9.1 (1H, m), 9.4~9.7 (1H, m)

(4) 7-[2-(2-Propynyloxyimino)-2-(5-amino-1,2,4-thiadiazol-3-yl)acetamido]-3-(3-formamido-1-pyridiniomethyl)-3-cephem-4-carboxylate (syn isomer), mp 163° to 168° C. (dec.).

I.R. (Nujol): 3400~3100, 1770, 1670, 1610, 1560~1500 cm$^{-1}$

N.M.R. (DMSO-d$_6$+D$_2$O, δ): 3.05 (1H, t, J=2 Hz), 3.15 and 3.70 (2H, ABq, J=18 Hz), 4.87 (2H, d, J=2 Hz), 5.23 (1H, d, J=5 Hz), 5.27 and 5.63 (2H, ABq, J=14 Hz), 5.84 (1H, d, J=5 Hz), 7.9~8.1 (1H, m), 8.42 (1H, s), 8.3~8.8 (2H, m), 9.4~9.5 (1H, m)

(5) 7-[2-(2-Propynyloxyimino)-2-(5-amino-1,2,4-thiadiazol-3-yl)acetamido]-3-(3-amino-1-pyridiniomethyl)-3-cephem-4-carboxylate (syn isomer), mp 158° to 170° C. (dec.).

I.R. (Nujol): 3350~3150, 1770, 1660~1590, 1510 cm$^{-1}$

N.M.R. (D$_2$O, δ): 3.15 and 3.67 (2H, ABq, J=18 Hz), 4.90 (2H, s), 5.0~5.6 (2H, m), 5.28 (1H, d, J=5 Hz), 5.88 (1H, d, J=5 Hz), 7.6~7.7 (2H, m), 8.0~8.2 (2H, m)

(6) 7-[2-Carboxymethoxyimino-2-(5-amino-1,2,4-thiadiazol-3-yl)acetamido]-3-(3-formamido-1-pyridiniomethyl)-3-cephem-4-carboxylate (syn isomer), mp 165° to 170° C. (dec.).

I.R. (Nujol): 3400~3100, 1770, 1670, 1630~1590, 1560, 1530, 1505 cm$^{-1}$

N.M.R. (D$_2$O, δ): 3.15 and 3.71 (2H, ABq, J=18 Hz), 4.73 (2H, s), 5.26 (1H, d, J=5 Hz), 5.27 and 5.65 (2H, ABq, J=14 Hz), 5.87 (1H, d, J=5 Hz), 7.9~8.1 (1H, m), 8.42 (1H, s), 8.3~8.8 (2H, m), 9.4~9.5 (1H, m)

(7) 7-[2-Carboxymethoxyimino-2-(5-amino-1,2,4-thiadiazol-3-yl)acetamido]-3-(3-amino-1-pyridiniomethyl)-3-cephem-4-carboxylate (syn isomer), mp 175° to 185° C. (dec.).

I.R. (Nujol): 3350, 3200, 1770, 1670~1590, 1510, 1230 cm$^{-1}$

N.M.R. (D$_2$O+NaHCO$_3$, δ): 3.17 and 3.61 (2H, ABq, J=18 Hz), 4.68 (2H, s), 5.25 (2H, broad s), 5.33 (1H, d, J=5 Hz), 5.90 (1H, d, J=5 Hz), 7.7 (2H, m), 8.1 (1H, m), 8.21 (1H, m)

(8) 7-[2-Methoxyimino-2-(5-amino-1,2,4-thiadiazol-3-yl)acetamido]-3-(4-hydroxymethyl-1-pyridiniomethyl)-3-cephem-4-carboxylate (syn isomer), mp. 152° to 156° C. (dec.).

IR (Nujol): 3650–3100, 1770, 1660, 1640, 1610, 1520 cm$^{-1}$

NMR (D$_2$O, δ): 3.18 and 3.72 (2H, ABq, J=18 Hz), 4.05 (3H,s), 4.97 (2H, s), 5.30 (1H, d, J=5 Hz), 5.30 and 5.60 (2H, ABq, J=14 Hz), 5.90 (1H, d, J=5 Hz), 8.02 (2H, d, J=7 Hz), 8.87 (2H, d, J=7 Hz)

(9) 7-[2-Methoxyimino-2-(5-amino-1,2,4-thiadiazol-3-yl)acetamido]-3-(3-hydroxymethyl-1-pyridiniomethyl)-3-cephem-4-carboxylate (syn isomer), mp. 164° to 168° C. (dec.).

IR (Nujol): 3650–3100, 1770, 1660, 1610, 1530, 1510 cm$^{-1}$

NMR (D$_2$O, δ): 3.18 and 3.72 (2H, ABq, J=18 Hz), 4.07 (3H, s), 4.70 (2H, s), 5.32 (1H, d, J=5 Hz), 5.32 and 5.65 (2H, ABq, J=14 Hz), 5.92 (1H, d, J=5 Hz), 8.13 (1H, m), 8.57 (1H, m), 8.70 (1H, m), 8.95 (1H, broad s)

(10) 7-[2-Methoxyimino-2-(5-amino-1,2,4-thiadiazol-3-yl)acetamido]-3-[4-(3-hydroxypropyl)-1-pyridiniomethyl]-3-cephem-4-carboxylate (syn isomer), mp. 115° to 120° C. (dec.).

IR (Nujol): 3400–3100, 1770, 1660, 1630, 1605, 1520 cm$^{-1}$

NMR (D$_2$O, δ): 2.00 (2H, m), 3,00 (2H, t, J=6.5 Hz), 3.0–3.8 (2H, m), 3.62 (2H, t, J=6.5 Hz), 4.02 (3H, s), 5.21 and 5.53 (2H, ABq, J=15 Hz), 5.23 (1H, d, J=5 Hz), 5.84 (1H, d, J=5 Hz), 7.87 (2H, d, J=7 Hz), 8.74 (2H, d, J=7 Hz)

(11) 7-[2-Ethoxyimino-2-(5-amino-1,2,4-thiadiazol-3-yl)acetamido]-3-(3-carboxy-1-pyridiniomethyl)-3-cephem-4-carboxylate (syn isomer), mp. 159° to 166° C. (dec.).

IR (Nujol): 3300, 3150, 3050, 1770, 1670, 1630, 1520 cm$^{-1}$

NMR (D$_2$O, δ): 1.27 (3H, t, J=7 Hz), 3.25 and 3.70 (2H, ABq, J=18 Hz), 4.32 (2H, q, J=7 Hz), 5.28 (1H, d, J=5 Hz), 5.38 and 5.73 (2H, ABq, J=14 Hz), 5.88 (1H, d, J=5 Hz), 8.15 (1H, m), 9.03 (2H, m), 9.40 (1H, broad s)

(12) 7-[2-Ethoxyimino-2-(5-amino-1,2,4-thiadiazol-3-yl)acetamido]-3-(4-formamido-1-pyridiniomethyl)-3-cephem-4-carboxylate (syn isomer), mp. 158° to 165° C. (dec.).

IR (Nujol): 3280, 3160, 1770, 1710, 1660, 1630, 1600, 1530, 1515 cm$^{-1}$

MNR (D$_2$O, δ): 1.30 (3H, t, J=7 Hz), 3.13 and 3.67 (2H, ABq, J=18 Hz), 4.30 (2H, q, J=7 Hz), 5.1–5.5 (3H, m), 5.83 (1H, d, J=5 Hz), 7.97 (2H, d, J=7 Hz), 8.67 (1H, broad s), 8.73 (2H, d, J=7 Hz)

EXAMPLE 19

A mixture of sodium 7-[2-methoxyimino-2-(5-amino-1,2,4-thiadiazol-3-yl)acetamido]cephalosporanate (syn isomer) (12.0 g), 3-methylpyridine (4.68 g), sodium iodide (44.4 g), phosphoric acid (1.48 g), water (7.3 ml) and acetonitrile (22.4 ml) was stirred for one hour at 72° to 76° C. The reaction mixture was diluted to 300 ml with water, adjusted to pH 3 with 6N hydrochloric acid and washed with ethyl acetate. The aqueous solution was separated out and subjected to column chromatography on a non ionic adsorption resin "Diaion HP-20" (Trademark: prepared by Mitsubishi Chemical Industries) (360 ml). After the column was washed with water, the elution was carried out with 25% aqueous methanol. The fractions containing an object compound were collected and concentrated to 20 ml under reduced pressure. The aqueous solution was mixed with N,N-dimethylformamide (20 ml) and the mixture was added to acetone (470 ml) under stirring. A resulting precipitate was filtered, washed with acetone and dried. The precipitate was dissolved in water (80 ml), passed through acidic alumina (22.5 g) and lyophilized to give 7-[2-methoxyimino-2-(5-amino-1,2,4-thiadiazol-3-yl)acetamido]-3-(3-methyl-1-pyridiniomethyl)-3-cephem-4-carboxylate (syn isomer) (4.81 g), mp. 150° to 154° C. (dec.).

IR (Nujol): 3650–3100, 1770, 1670, 1640–1610, 1520 cm$^{-1}$

NMR (D$_2$O, δ): 2.52 (3H, s), 3.15 and 3.65 (2H, ABq, J=18 Hz), 4.02 (3H, s), 5.27 (1H, d, J=5 Hz), 5.25 and 5.55 (2H, ABq, J=14 Hz), 5.87 (1H, d, J=5 Hz), 7.73–8.10 (1H, m), 8.23–8.50 (1H, m), 8.63–8.83 (1H, m)

EXAMPLE 20

The following compounds were obtained according to similar manners to those of aforesaid Examples.

(1) 7-[2-Methoxyimino-2-(5-amino-1,2,4-thiadiazol-3-yl)acetamido]-3-(4-methyl-1-pyridiniomethyl)-3-cephem-4-carboxylate (syn isomer), mp. 155° to 160° C. (dec.).

IR (Nujol): 3650–3100, 1770, 1660, 1640, 1610, 1520 cm$^{-1}$

NMR (D$_2$O, δ): 2.63 (3H, s), 3.15 and 3.67 (2H, ABq, J=18 Hz), 4.03 (3H, s), 5.27 (1H, d, J=5 Hz), 5.22 and 5.55 (2H, ABq, J=14 Hz), 5.85 (1H, d, J=5 Hz), 7.83 (2H, d, J=7 Hz), 8.73 (2H, d, J=7 Hz)

(2) 7-[2-Methoxyimino-2-(5-amino-1,2,4-thiadiazol-3-yl)acetamido]-3-(3-methyl-1-pyridiniomethyl)-3-cephem-4-carboxylate (syn isomer), mp. 150° to 154° C. (dec.).

IR (Nujol): 3650–3100, 1770, 1670, 1640–1610, 1520 cm$^{-1}$

NMR (D$_2$O, δ): 2.52 (3H, s), 3.15 and 3.65 (2H, ABq, J=18 Hz), 4.02 (3H, s), 5.27 (1H, d, J=5 Hz), 5.25 and 5.55 (2H, ABq, J=14 Hz), 5.87 (1H, d, J=5 Hz), 7.73–8.10 (1H, m), 8.23–8.50 (1H, m), 8.63–8.83 (1H, m)

(3) 7-[2-Methoxyimino-2-(5-amino-1,2,4-thiadiazol-3-yl)acetamido]-3-(3-ethyl-1-pyridiniomethyl)-3-cephem-4-carboxylate (syn isomer), mp. 160° to 165° C. (dec.).

IR (Nujol): 3300, 3150, 1770, 1670, 1610, 1530, 1285, 1140, 1040 cm$^{-1}$

NMR (D$_2$O, δ): 1.30 (3H, t, J=7 Hz), 2.92 (2H, q, J=7 Hz), 3.22 and 3.68 (2H, ABq, J=18 Hz), 4.05 (3H, s), 5.28 (1H, d, J=5 Hz), 5.28 and 5.58 (2H, ABq, J=14 Hz), 5.88 (1H, d, J=5 Hz) 7.82–8.13 (1H, m), 8.30–8.57 (1H, m), 8.63–8.90 (2H, m)

(4) 7-[2-Ethoxyimino-2-(5-amino-b 1,2,4-thiadiazol-3-yl)acetamido]-3-(3-ethyl-1-pyridiniomethyl)-3-cephem-4-carboxylate (syn isomer), mp. 150° to 155° C. (dec.).

IR (Nujol): 3250, 3150, 1770, 1670, 1610, 1530, 1510, 1290, 1150, 1040 cm$^{-1}$ NMR (D$_2$O, δ): 1.30 (6H, t, J=7 Hz), 2.93 (2H, q, J=7 Hz), 3.17 and 3.68 (2H, ABq, J=18 Hz), 4.37 (2H, q, J=7 Hz), 5.30 (1H, d, J=5 Hz), 5.28 and 5.58 (2H, ABq, J=14 Hz), 5.88 (1H, d, J=5 Hz), 7.80–8.15 (1H, m), 8.30–8.60 (1H, m), 8.65–8.92 (2H, m)

(5) 7-[2-Ethoxyimino-2-(5-amino-1,2,4-thiadiazol-3-yl)acetamido]-3-[2-(2-hydroxyethyl)-1-pyridiniomethyl]-3-cephem-4-carboxylate (syn isomer), mp. 150° to 155° C. (dec.).

IR (Nujol): 3650–3100, 1770, 1660, 1620, 1530, 1280, 1180, 1140, 1040 cm$^{-1}$

NMR (D$_2$O, δ): 1.32 (3H, t, J=7 Hz), 3.15 and 3.62 (2H, ABq, J=18 Hz), 3.43 (2H, t, J=6 Hz), 4.07 (2H, t, J=6 Hz), 4.40 (2H, q, J=7 Hz), 5.30 (1H, d, J=5 Hz), 5.57 (2H, m), 5.90 (1H, d, J=5 Hz), 7.63–8.30 (2H, m), 8.33–8.70 (1H, m), 8.85 (1H, d, J=6 Hz)

(6) 7-[2-Methoxyimino-2-(5-amino-1,2,4-thiadiazol-3-yl)acetamido]-3-[2-(2-hydroxyethyl)-1-pyridiniomethyl]-3-cephem-4-carboxylate (syn isomer), mp. 160° to 165° C. (dec.).

IR (Nujol): 3650–3100, 1770, 1660, 1620, 1520, 1280, 1170, 1140, 1040 cm$^{-1}$

NMR (D$_2$O, δ): 3.15 and 3.58 (2H, ABq, J=18 Hz), 3.43 (2H, t, J=6 Hz), 4.07 (3H, s), 4.07 (2H, t, J=6 Hz), 5.27 (1H, d, J=5 Hz), 5.57 (2H, m), 5.90 (1H, d, J=5 Hz), 7.70–8.13 (2H, m), 8.23–8.63 (1H, m), 8.80 (1H, d, J=6 Hz)

(7) 7-[2-Methoxyimino-2-(5-amino-1,2,4-thiadiazol-3-yl)acetamido]-3-(2-methyl-1-pyridiniomethyl)-3-cephem-4-carboxylate (syn isomer), mp. 150° to 154° C. (dec.).

IR (Nujol): 3650–3100, 1770, 1670, 1630, 1610, 1530, 1290, 1150, 1040 cm$^{-1}$

NMR (D$_2$O, δ): 2.83 (3H, s), 3.15 and 3.57 (2H, ABq, J=18 Hz), 4.05 (3H, s), 5.27 (1H, d, J=5 Hz), 5.28 and 5.57 (2H, ABq, J=14 Hz), 5.87 (1H, d, J=5 Hz), 7.68–8.00 (2H, m), 8.17–8.57 (1H, m), 8.72 (1H, d, J=6 Hz)

(8) 7-[2-Ethoxyimino-2-(5-amino-1,2,4-thiadiazol-3-yl)acetamido]-3-[3-(3-hydroxypropyl)-1-pyridiniomethyl]-3-cephem-4-carboxylate (syn isomer), mp. 160° to 165° C. (dec.).

IR (Nujol): 3250, 3150, 1770, 1670, 1530, 1280, 1140, 1060, 1040 cm$^{-1}$

NMR (D$_2$O, δ): 1.30 (3H, t, J=7 Hz), 1.73–2.27 (2H, m), 2.70–3.13 (2H, m), 3.15 and 3.65 (2H, ABq, J=18 Hz), 3.63 (2H, t, J=7 Hz), 4.33 (2H, q, J=7 Hz), 5.30 (1H, d, J=5 Hz), 5.28 and 5.58 (2H, ABq, J=14 Hz), 5.88 (1H, d, J=5 Hz), 7.77–8.10 (1H, m), 8.40 (1H, broad d, J=8 Hz), 8.75 (1H, d, J=5 Hz), 8.80 (1H, s).

(9) 7-[2-Ethoxyimino-2-(5-amino-1,2,4-thiadiazol-3-yl)acetamido]-3-[4-(1-hydroxyethyl)-1-pyridiniomethyl]-3-cephem-4-carboxylate (syn isomer), mp. 160° to 165° C. (dec.).

IR (Nujol): 3250, 3150, 1770, 1660, 1640, 1610, 1520, 1280, 1150, 1100, 1040 cm$^{-1}$ NMR (D$_2$O, δ): 1.33 (3H, t, J=7 Hz), 1.60 (3H, d, J=7 Hz), 3.20 and 3.73 (2H, ABq, J=18 Hz), 4.40 (2H, q, J=7 Hz), 5.03–5.50 (1H, m), 5.33 (1H, d, J=5 Hz), 5.30 and 5.62 (2H, ABq, J=14 Hz), 5.93 (1H, d, J=5 Hz), 8.08 (2H, d, J=7 Hz), 8.93 (2H, d, J=7 Hz)

(10) 7-[2-Ethoxyimino-2-(5-amino-1,2,4-thiadiazol-3-yl)acetamido]-3-[3-(2-hydroxyethyl)-1-pyridiniomethyl]-3-cephem-4-carboxylate (syn isomer), mp. 155° to 160° C. (dec.).

IR (Nujol): 3250, 3170, 1770, 1660, 1610, 1530 cm$^{-1}$

NMR (D$_2$O, δ): 1.28 (3H, t, J=7 Hz), 3.07 (2H, t, J=6 Hz), 3.23 and 3.57 (2H, ABq, J=18 Hz), 3.90 (2H, t, J=6 Hz), 4.32 (2H, q, J=7 Hz), 5.27 (1H, d, J=5 Hz), 5.35 and 5.53 (2H, ABq, J=14 Hz), 5.87 (1H, d, J=5 Hz), 7.83–8.17 (1H, m), 8.33–8.60 (1H, m), 8.70–8.97 (2H, m)

(11) 7-[2-Methoxyimino-2-(5-amino-1,2,4-thiadiazol-3-yl)acetamido]-3-(3-chloro-1-pyridiniomethyl)-3-cephem-4-carboxylate (syn isomer), mp. 145° to 150° C. (dec.).

IR (Nujol): 3270, 3170, 1770, 1660, 1610, 1525, 1490 cm$^{-1}$

NMR (D$_2$O, δ): 3.25 and 3.68 (2H, ABq, J=18 Hz), 4.07 (3H, s), 5.28 (1H, d, J=5 Hz), 5.37 and 5.62 (2H, ABq, J=14 Hz), 5.88 (1H, d, J=5 Hz), 7.90–8.23 (1H, m), 8.50–8.77 (1H, m), 8.85–9.08 (1H, m), 9.18 (1H, broad s)

(12) 7-[2-Methoxyimino-2-(5-amino-1,2,4-thiadiazol-3-yl)acetamido]-3-(3,5-dimethyl-1-pyridiniomethyl)-3-cephem-4-carboxylate (syn isomer), mp. 146° to 150° C. (dec.).

IR (Nujol): 3400, 3300, 3200, 1770, 1665, 1610, 1530 cm$^{-1}$

NMR (D$_2$O, δ): 2.48 (6H, s), 3.22 and 3.55 (2H, ABq, J=18 Hz), 4.03 (3H, s), 5.25 (1H, d, J=5 Hz), 5.28 and 5.43 (2H, ABq, J=14 Hz), 5.85 (1H, d, J=5 Hz), 8.15 (1H, s), 8.60 (2H, s)

(13) 7-[2-Methoxyimino-2-(5-amino-1,2,4-thiadiazol-3-yl)acetamido]-3-[3-(3-hydroxypropyl)-1-pyridiniomethyl]-3-cephem-4-carboxylate (syn isomer), mp. 163° to 167° C. (dec.).

IR (Nujol): 3250, 3150, 1770, 1660, 1610, 1525 cm$^{-1}$

NMR (D$_2$O, δ): 1.7–2.23 (2H, m), 2.73–3.17 (2H, m), 3.23 and 3.60 (2H, ABq, J=18 Hz), 3.63 (2H, t, J=7 Hz), 4.05 (3H, s), 5.27 (1H, d, J=5 Hz), 5.37 and 5.53 (2H, ABq, J=14 Hz), 5.87 (1H, d, J=5 Hz), 7.80–8.17 (1H, m), 8.23–8.60 (1H, m), 8.67–8.93 (2H, m).

(14) 7-[2-Ethoxyimino-2-(5-amino-1,2,4-thiadiazol-3-yl)acetamido]-3-(3-oxaloamino-1-pyridiniomethyl)-3-cephem-4-carboxylate (syn isomer), mp. 108.5° to 117.5° C.

IR (Nujol): 3250, 1770, 1660, 1590, 1530, 1180, 1145, 1040 cm$^{-1}$

NMR (D$_2$O, δ): 1.33 (3H, t, J=7 Hz), 3.33 and 3.73 (2H, ABq, J=18 Hz), 4.35 (2H, q, J=7 Hz), 5.22 (1H, d, J=5 Hz), 5.32 and 5.70 (2H, ABq, J=14 Hz) 5.92 (1H, d, J=5 Hz), 8.05 (1H, m), 8.45 (1H, m), 8.75 (1H, m), 9.53 (1H, m)

(15) 7-[2-Ethoxyimino-2-(5-amino-1,2,4-thiadiazol-3-yl)acetamido]-3-(3-formamidomethyl-1-pyridiniomethyl)-3-cephem-4-carboxylate (syn isomer), mp. 157° to 161° C. (dec.)

IR (Nujol): 3250, 3200, 3050, 1775, 1660, 1610, 1530, 1350, 1285, 1140, 1060, 1035 cm$^{-1}$ NMR (D$_2$O, δ): 1.30 (3H, t, J=7 Hz), 3.18 and 3.62 (2H, ABq, J=18 Hz), 4.30 (2H, q, J=7 Hz), 4.62 (2H, s), 5.25 (1H, d, J=5 Hz), 5.30 and 5.57 (2H, ABq, J=14 Hz), 5.85 (1H, d, J=5 Hz), 8.00 (1H, dd, J=6 and 8 Hz), 8.20 (1H, s), 8.45 (1H, d, J=8 Hz), 8.85 (1H, d, J=6 Hz), 8.89 (1H, s)

(16) 7-[2-Ethoxyimino-2-(5-amino-1,2,4-thiadiazol-3-yl)acetamido]-3-(4-amino-1-pyridiniomethyl)-3-cephem-4-carboxylate (syn isomer), mp. 165° to 175° C. (dec.).

IR (Nujol): 3300, 3150, 1770, 1650, 1600, 1530, 1160, 1035 cm$^{-1}$

NMR (D$_2$O, δ): 1.32 (3H, t, J=7 Hz), 3.15 and 3.65 (2H, ABq, J=18 Hz), 4.35 (2H, q, J=7 Hz), 5.00 (2H, broad s), 5.26 (1H, d, J=5 Hz), 5.88 (1H, d, J=5 Hz), 6.94 (2H, d, J=7 Hz), 8.08 (2H, d, J=7 Hz).

(17) 7-[2-Allyloxyimino-2-(5-amino-1,2,4-thiadiazol-3-yl)acetamido]-3-(3,5-dimethyl-1-pyridiniomethyl)-3-cephem-4-carboxylate (syn isomer), mp. 198° to 203° C. (dec.).

IR (Nujol): 3250, 3160, 1770, 1665, 1610, 1525, 1290, 1170, 1150, 1060, 1010 cm$^{-1}$ NMR (D$_2$O, δ): 2.48 (6H, s), 3.15 and 3.60 (2H, ABq, J=18 Hz), 4.7–4.9 (2H, m), 5.25 (1H, d, J=5 Hz), 4.9–5.7 (4H, m), 5.75–6.40 (1H, m), 5.87 (1H, d, J=5 Hz), 8.15 (1H, s), 8.57 (2H, s)

(18) 7-[2-Allyloxyimino-2-(5-amino-1,2,4-thiadiazol-3-yl)acetamido]-3-(3-ethyl-1-pyridiniomethyl)-3-cephem-4-carboxylate (syn isomer), mp. 195° to 200° C. (dec.).

IR (Nujol): 3270, 3160, 1770, 1665, 1610, 1530, 1280, 1145, 1060 cm$^{-1}$

NMR (D$_2$O, δ): 1.28 (3H, t, J=7 Hz), 2.86 (2H, q, J=7 Hz), 3.17 and 3.58 (2H, ABq, J=18 Hz), 4.6–4.8 (2H, m), 5.25 (1H, d, J=5 Hz), 5.1–5.8 (4H, m), 5.90 (1H, d, J=5 Hz), 5.8–6.5 (1H, m), 7.8–8.1 (1H, m), 8.2–8.6 (1H, m), 8.7–8.9 (1H, m), 8.80 (1H, s)

(19) 7-[2-(2-Propynyloxyimino)-2-(5-amino-1,2,4-thiadiazol-3-yl)acetamido]-3-(3,5-dimethyl-1-pyridiniomethyl)-3-cephem-4-carboxylate (syn isomer), mp. 175° to 180° C. (dec.).

IR (Nujol): 3400, 3250, 3050, 2110, 1775, 1660, 1610, 1530 cm$^{-1}$

NMR (DMSO-d$_6$+D$_2$O, δ): 2.47 (6H, s), 3.43 (1H, t, J=2 Hz), 3.12 and 3.45 (2H, ABq, J=18 Hz), 4.73 (1H, d, J=2 Hz), 5.03 (1H, d, J=5 Hz) 5.17 and 5.52 (2H, ABq, J=14 Hz), 5.68 (1H, d, J=5 Hz), 8.23 (1H, s), 9.00 (2H, s)

(20) 7[2-(2-propynyloxyimino)-2-(5-amino-1,2,4-thiadiazol-3-yl)acetamido]-3-(3-ethyl-1-pyridiniomethyl)-3-cephem-4-carboxylate (syn isomer), mp. 165° to 170° C. (dec.).

IR (Nujol): 3400, 3250, 3150, 2090, 1770, 1660, 1610, 1520 cm$^{-1}$

NMR (DMSO-d$_6$+D$_2$O, δ): 1.33 (3H, t, J=7 Hz), 2.90 (2H, q, J=7 Hz), 3.17 and 3.55 (2H, ABq, J=18 Hz), 3.50 (1H, t, J=2 Hz), 4.80 (2H, d, J=2 Hz), 5.12 (1H, d, J=5 Hz), 5.25 and 5.67 (2H, ABq, J=14 Hz), 5.75 (1H, d, J=5 Hz), 7.93–8.23 (1H, m), 8.37–8.67 (1H, m), 9.17–9.40 (2H, m)

(21) 7-[2-(2-Cyclopenten-1-yloxyimino)-2-(5-amino-1,2,4-thiadiazol-3-yl)acetamido]-3-(3,5-dimethyl-1-pyridiniomethyl)-3-cephem-4-carboxylate (syn isomer).

IR (Nujol): 3300, 3170, 1770, 1670, 1610, 1525, 1290, 1170, 1060, 1030 cm$^{-1}$ NMR (D$_2$O, δ): 1.8–2.6 (4H, m), 2.42 (6H, s), 3.08 and 3.50 (2H, ABq, J=17 Hz), 4.95 (1H, m), 5.05–5.62 (2H, m), 5.15 (1H, d, J=5 Hz), 5.77 (1H, d, J=5 Hz), 5.85–6.12 (2H, m), 8.10 (1H, broad s), 8.50 (2H, broad s)

(22) 7-[2-(2-Cyclopenten-1-yloxyimino)-2-(5-amino-1,2,4-thiadiazol-3-yl)-acetamido]-3-(3-ethyl-1-pyridiniomethyl)-3-cephem-4-carboxylate (syn isomer), mp. 151° to 158° C. (dec.).

IR (Nujol): 3300, 3200, 1765, 1660, 1610, 1525, 1280, 1140, 1060, 1030 cm$^{-1}$ NMR (D$_2$O+acetone-d$_6$, δ): 1.30 (3H, t, J=7 Hz), 1.80–2.60 (4H, m), 2.92 (2H, q, J=7 Hz), 3.17 and 3.63 (2H, ABq, J=18 Hz), 4.67–6.27 (5H, m), 5.21 (1H, d, J=5 Hz), 5.85 (1H, d, J=5 Hz), 8.02 (1H, dd, J=6 and 8 Hz), 8.47 (1H, d, J=8 Hz), 8.95 (2H, m)

EXAMPLE 21

A powder of 7-[2-methoxyimino-2-(5-amino-1,2,4-thiadiazol-3-yl)acetamido]-3-(3,5-dimethyl-1-pyridiniomethyl)-3-cephem-4-carboxylate (syn isomer) (50 mg) was dissolved in water (25 ml) and allowed to stand for several days in a refrigerator. The resulting crystals were collected and used as seeding one.

A solution of 7-[2-methoxyimino-2-(5-amino-1,2,4-thiadiazol-3-yl)acetamido]-3-(3,5-dimethyl-1-pyridiniomethyl)-3-cephem-4-carboxylate (syn isomer) (1.58 g) in water (1.6 ml) was seeded with crystals of previously obtained sample and allowed to stand overnight in a refrigerator. The resulting crystals were collected by filtration, washed with cold water and dried to give colorless crystals of 7-[2-methoxyimino-2-(5-amino-1,2,4-thiadiazol-3-yl)acetamido]-3-(3,5-dimethyl-1-pyridiniomethyl)-3-cephem-4-carboxylate (syn isomer) (370 mg).

According to a similar manner to that of Example 21, the crystal forms of the compounds of the aforesaid Examples were also obtained.

What we claim is:

1. Cephem compounds of the formula:

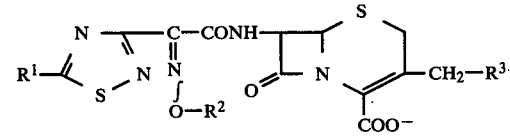

wherein
R$^1$ is amino or a protected amino group;
R$^2$ is lower alkyl, lower alkenyl, lower alkynyl or cyclo (lower) alkenyl; and
R$^3$ is a pyridino group substituted with 1 to 2 substituent(s) selected from the group consisting of halogen, amino, acylamino, lower alkyl, hydroxy (lower) alkyl and protected amino (lower) alkyl.

2. Syn isomer of a compound of claim 1.

3. A pharmaceutical antibacterial composition comprising an antimicrobially effective amount of a compound of claim 1 in association with a pharmaceutically acceptable, substantially non-toxic carrier or excipient.

4. A compound of claim 2, wherein R$^3$ is a pyridinio group substituted with 1 to 2 substituent(s) selected from the group consisting of halogen, amino, lower alkanoylamino substituted with carboxy, lower alkyl, hydroxy(lower)alkyl and lower alkanoylamino(lower)alkyl.

5. A compound of claim 4, wherein R$^2$ is methyl, ethyl, allyl, 2-propynyl or 2-cyclopenten-1-yl and R$^3$ is a pyridinio group substituted with 1 to 2 substituent(s)

selected from the group consisting of chlorine, amino, oxaloamino, methyl, ethyl, hydroxyethyl, hydroxypropyl, and formamidomethyl.

6. A compound of claim 5, which is selected from the group consisting of:
7-[2-methoxyimino-2-(5-amino-1,2,4-thiadiazol-3-yl)acetamido]-3-(3-methyl-1-pyridiniomethyl)-3-cephem-4-carboxylate (syn isomer),
7-[2-methoxyimino-2-(5-amino-1,2,4-thiadiazol-3-yl)acetamido]-3-(4-methyl-1-pyridiniomethyl)-3-cephem-4-carboxylate (syn isomer),
7-[2-ethoxyimino-2-(5-amino-1,2,4-thiadiazol-3-yl)acetamido]-3-(4-amino-1-pyridiniomethyl)-3-cephem-4-carboxylate (syn isomer),
7-[2-methoxyimino-2-(5-amino-1,2,4-thiadiazol-3-yl)acetamido]-3-(3-ethyl-1-pyridiniomethyl)-3-cephem-4-carboxylate (syn isomer),
7-[2-ethoxyimino-2-(5-amino-1,2,4-thiadiazol-3-yl)acetamido]-3-(3-ethyl-1-pyridiniomethyl)-3-cephem-4-carboxylate (syn isomer),
7-[2-methoxyimino-2-(5-amino-1,2,4-thiadiazol-3-yl)acetamido]-3-[2-(2-hydroxyethyl)-1-pyridiniomethyl]-3-cephem-4-carboxylate (syn isomer),
7-[2-ethoxyimino-2-(5-amino-1,2,4-thiadiazol-3-yl)acetamido]-3-[2-(2-hydroxyethyl)-1-pyridiniomethyl]-3-cephem-4-carboxylate (syn isomer),
7-[2-methoxyimino-2-(5-amino-1,2,4-thiadiazol-3-yl)acetamido]-3-(2-methyl-1-pyridiniomethyl)-3-cephem-4-carboxylate (syn isomer),
7-[2-ethoxyimino-2-(5-amino-1,2,4-thiadiazol-3-yl)acetamido]-3-[3-(3-hydroxypropyl)-1-pyridiniomethyl]-3-cephem-4-carboxylate (syn isomer),
7-[2-ethoxyimino-2-(5-amino-1,2,4-thiadiazol-3-yl)acetamido]-3-[4-(1-hydroxyethyl)-1-pyridiniomethyl]-3-cephem-4-carboxylate (syn isomer),
7-[2-ethoxyimino-2-(5-amino-1,2,4-thiadiazol-3-yl)acetamido]-3-[3-(2-hydroxyethyl)-1-pyridiniomethyl]-3-cephem-4-carboxylate (syn isomer),
7-[2-methoxyimino-2-(5-amino-1,2,4-thiadiazol-3-yl)acetamido]-3-(3-chloro-1-pyridiniomethyl)-3-cephem-4-carboxylate (syn isomer),
7-[2-methoxyimino-2-(5-amino-1,2,4-thiadiazol-3-yl)acetamido]-3-(3,5-dimethyl-1-pyridiniomethyl)-3-cephem-4-carboxylate (syn isomer),
7-[2-methoxyimino-2-(5-amino-1,2,4-thiadiazol-3-yl)acetamido]-3-[3-(3-hydroxypropyl)-1-pyridiniomethyl]-3-cephem-4-carboxylate (syn isomer),
7-[2-ethoxyimino-2-(5-amino-1,2,4-thiadiazol-3-yl)acetamido]-3-(3-oxaloamino-1-pyridiniomethyl)-3-cephem-4-carboxylate (syn isomer),
7-[2-ethoxyimino-2-(5-amino-1,2,4-thiadiazol-3-yl)acetamido]-3-(3-form-amidomethyl-1-pyridiniomethyl)-3-cephem-4-carboxylate (syn isomer),
7-[2-allyloxyimino-2-(5-amino-1,2,4-thiadiazol-3-yl)acetamido]-3-(3,5-dimethyl-1-pyridiniomethyl)-3-cephem-4-carboxylate (syn isomer),
7-[2-(2-propynyloxyimino)-2-(5-amino-1,2,4-thiadiazol-3-yl)acetamido]-3-(3,5-dimethyl-1-pyridiniomethyl)-3-cephem-4-carboxylate (syn isomer),
7-[2-allyloxyimino-2-(5-amino-1,2,4-thiadiazol-3-yl)acetamido]-3-(3-ethyl-1-pyridiniomethyl)-3-cephem-4-carboxylate (syn isomer),
7-[2-(2-propynyloxyimino)-2-(5-amino-1,2,4-thiadiazol-3-yl)acetamido]-3-(3-ethyl-1-pyridiniomethyl)-3-cephem-4-carboxylate (syn isomer),
7-[2-(2-cyclopenten-1-yloxyimino)-2-(5-amino-1,2,4-thiadiazol-3-yl)acetamido]-3-(3,5-dimethyl-1-pyridiniomethyl)-3-cephem-4-carboxylate (syn isomer) and
7-[2-(2-cyclopenten-1-yloxyimino)-2-(5-amino-1,2,4-thiadiazol-3-yl)acetamido]-3-(3-ethyl-1-pyridiniomethyl)-3-cephem-4-carboxylate (syn isomer).

7. A compound of claim 6, which is 7-[2-methoxyimino-2-(5-amino-1,2,4-thiadiazol-3-yl)acetamido]-3-(3-methyl-1-pyridiniomethyl)-3-cephem-4-carboxylate (syn isomer).

8. A compound of claim 6, which is 7-[2-methoxyimino-2-(5-amino-1,2,4-thiadiazol-3-yl)acetamido]-3-(4-methyl-1-pyridiniomethyl)-3-cephem-4-carboxylate (syn isomer).

9. A compound of claim 6, which is 7-[2-ethoxyimino-2-(5-amino-1,2,4-thiadiazol-3-yl)acetamido]-3-(4-amino-1-pyridiniomethyl)-3-cephem-4-carboxylate (syn isomer).

10. A compound of claim 6, which is 7-[2-methoxyimino-2-(5-amino-1,2,4-thiadiazol-3-yl)acetamido]-3-(3-ethyl-1-pyridiniomethyl)-3-cephem-4-carboxylate (syn isomer).

11. A compound of claim 6, which is 7-[2-ethoxyimino-2-(5-amino-1,2,4-thiadiazol-3-yl)acetamido]-3-(3-ethyl-1-pyridiniomethyl)-3-cephem-4-carboxylate (syn isomer).

12. A compound of claim 6, which is 7-[2-methoxyimino-2-(5-amino-1,2,4-thiadiazol-3-yl)acetamido]-3-[2-(2-hydroxyethyl-1-pyridiniomethyl]-3-cephem-4-carboxylate (syn isomer).

13. A compound of claim 6, which is 7-[2-ethoxyimino-2-(5-amino-1,2,4-thiadiazol-3-yl)acetamido]-3-[2-(2-hydroxyethyl)-1-pyridiniomethyl]-3-cephem-4-carboxylate (syn isomer).

14. A compound of claim 6, which is 7-[2-methoxyimino-2-(5-amino-1,2,4-thiadiazol-3-yl)acetamido]-3-(2-methyl-1-pyridiniomethyl)-3-cephem-4-carboxylate (syn isomer).

15. A compound of claim 6, which is 7-[2-ethoxyimino-2-(5-amino-1,2,4-thiadiazol-3-yl)acetamido]-3-[3-(3-hydroxypropyl-1-pyridiniomethyl)-3-cephem-4-carboxylate (syn isomer).

16. A compound of claim 6, which is 7-[2-ethoxyimino-2-(5-amino-1,2,4-thiadiazol-3-yl)acetamido]-3-[4-(1-hydroxyethyl-1-pyridiniomethyl)-3-cephem-4-carboxylate (syn isomer).

17. A compound of claim 6, which is 7-[2-ethoxyimino-2-(5-amino-1,2,4-thiadiazol-3-yl)acetamido]-3-[3-(2-hydroxyethyl)-1-pyridiniomethyl]-3-cephem-4-carboxylate (syn isomer).

18. A compound of claim 6, which is 7-[2-methoxyimino-2-(5-amino-1,2,4-thiadiazol-3-yl)acetamido]-3-(3-chloro-1-pyridiniomethyl)-3-cephem-4-carboxylate (syn isomer).

19. A compound of claim 6, which is 7-[2-methoxyimino-2-(5-amino-1,2,4-thiadiazol-3-yl)acetamido]-3-(3,5-dimethyl-1-pyridiniomethyl)-3-cephem-4-carboxylate (syn isomer).

20. A compound of claim 6, which is 7-[2-methoxyimino-2-(5-amino-1,2,4-thiadiazol-3-yl)acetamido]-3-[3-(3-hydroxypropyl-1-pyridiniomethyl)-3-cephem-4-carboxylate (syn isomer).

21. A compound of claim 6, which is 7-[2-ethoxyimino-2-(5-amino-1,2,4-thiadiazol-3-yl)acetamido]-3-(3-oxaloamino-1-pyridiniomethyl)-3-cephem-4-carboxylate (syn isomer).

22. A compound of claim 6, which is 7-[2-allyloxyimino-2-(5-amino-1,2,4-thiadiazol-3-yl)acetamido]-3-

(3,5-dimethyl-1-pyridiniomethyl)-3-cephem-4-carboxylate (syn isomer).

23. A compound of claim 6, which is 7-[2-(2-propynyloxyimino)-2-(5-amino-1,2,4-thiadiazol-3-yl)acetamido]-3-(3,5-dimethyl-1-pyridiniomethyl)-3-cephem-4-carboxylate (syn isomer).

24. A compound of claim 6, which is 7-[2-allyloxyimino-2-(5-amino-1,2,4-thiadiazol-3-yl)acetamido]-3-(3-ethyl-1-pyridiniomethyl)-3-cephem-4-carboxylate (syn isomer).

25. A compound of claim 6, which is 7-[2-(2-propynyloxyimino)-2-(5-amino-1,2,4-thiadiazol-3-yl)acetamido]-3-(3-ethyl-1-pyridiniomethyl)-3-cephem-4-carboxylate (syn isomer).

26. A compound of claim 6, which is 7-[2-(2-cyclopenten-1-yloxyimino)-2-(5-amino-1,2,4-thiadiazol-3-yl)-acetamido]-3-(3,5-dimethyl-1-pyridiniomethyl)-3-cephem-4-carboxylate (syn isomer).

27. A compound of claim 6, which is 7-[2-(2-cyclopenten-1-yloxyimino)-2-(5-amino-1,2,4-thiadiazol-3-yl)-acetamido]-3-(3-ethyl-1-pyridiniomethyl)-3-cephem-4-carboxylate (syn isomer).

* * * * *

UNITED STATES PATENT AND TRADEMARK OFFICE
CERTIFICATE OF CORRECTION

PATENT NO. : 4,457,928

DATED : July 3, 1984

INVENTOR(S) : Teraji et al.

It is certified that error appears in the above-identified patent and that said Letters Patent is hereby corrected as shown below:

On the title page:

- - [75] Tsutomu Teraji, Osaka; Kazuo Sakane; Amagasaki; Jiro Goto, Suita, all of Japan - -

*Signed and Sealed this*

*Nineteenth* Day of *February 1985*

[SEAL]

*Attest:*

DONALD J. QUIGG

*Attesting Officer*  *Acting Commissioner of Patents and Trademarks*